United States Patent
Wang et al.

(10) Patent No.: US 6,927,321 B2
(45) Date of Patent: Aug. 9, 2005

(54) ARCELIN-5 PROMOTER AND USES THEREOF

(75) Inventors: Qi Wang, St. Louis, MO (US); Patrice Dubois, Richmond Heights, MO (US); Jihong Liang, Chesterfield, MO (US); Tim Oulmassov, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 505 days.

(21) Appl. No.: 10/015,637

(22) Filed: Dec. 17, 2001

(65) Prior Publication Data

US 2003/0046727 A1 Mar. 6, 2003

Related U.S. Application Data

(60) Provisional application No. 60/255,879, filed on Dec. 18, 2000.

(51) Int. Cl.[7] .......................... C12N 5/82; C12N 15/29; C12N 15/11; C12N 5/04; A01H 5/00
(52) U.S. Cl. .................... 800/287; 536/24.1; 536/23.6; 435/426; 435/419; 435/415; 800/312; 800/278
(58) Field of Search .............................. 536/23.1, 24.1, 536/23.6; 435/426, 419; 800/312, 278, 287

(56) References Cited

U.S. PATENT DOCUMENTS

| | | | |
|---|---|---|---|
| 3,959,493 A | 5/1976 | Baalsrud et al. | |
| 4,533,557 A | 8/1985 | Maruyama et al. | |
| 4,554,101 A | 11/1985 | Hopp | |
| 4,683,195 A | 7/1987 | Mullis et al. | |
| 4,683,202 A | 7/1987 | Mullis | |
| 4,713,245 A | 12/1987 | Ando et al. | |
| 4,757,011 A | 7/1988 | Chaleff et al. | |
| 4,769,061 A | 9/1988 | Comai | |
| 4,826,694 A | 5/1989 | McAskie | |
| 4,940,835 A | 7/1990 | Shah et al. | |
| 4,971,908 A | 11/1990 | Kishore et al. | |
| 5,110,732 A | * 5/1992 | Benfey et al. ............... | 800/287 |
| 5,384,253 A | 1/1995 | Krzyzek et al. | |
| 5,689,052 A | 11/1997 | Brown et al. | |

FOREIGN PATENT DOCUMENTS

| | | |
|---|---|---|
| EP | 0 218 571 B1 | 4/1987 |
| EP | 0 255 378 B2 | 2/1988 |
| EP | 0 385 962 B1 | 9/1990 |
| EP | 0 154 204 B1 | 1/1994 |
| WO | WO 02/00899 A2 | 6/2000 |

OTHER PUBLICATIONS

Tisserat, in Plant Cell Culture, ed R.A. Dixon, 1985, IRL Press, Oxford, pp. 79–105, especially p. 80, Table 1, p. 82, and Table 4, pp. 85–90.*
Kuo et. al., Journal of Plant Nutrition, 1994, vol. 17, No. 4, pp. 549–560.*
Goossens, et. al., Plant Physiol., Aug. 1999, vol. 120, pp. 1095–110 (IDS) and NCBI accession Z50202, Aug. 1998.*
Chee et. al. Transformation of Soybean (Glycine max) via Agrobacterium tumefaciens and analysis of transformed plants, in Methods in Molecular biology, 1995, vol. 44, Humana Press Inc, Totowa, NJ, pp. 101–119.*
Andres et al., *Bean Arcelin (1) Inheritance of a novel seed protein of Phaseolus vlugaris L. and its effect on seed composition*, Theor Appl Genet, 72:123–128 (1986).
Goossens et al., *Isolation and characterisation of acrelin–5 proteins and cDNAs*, Eur J Biochem, 225:787–795 (1994).
Goossens et al., *The arcelin–5 Gene of Phaseolus vulgaris Directs High Speed–Specific Expression in Transfenic Phaseolus acutifolius and Arabidopsis Plants*, Plant Physiology, 120:1095–1104 (1999).
Cho et al., *Expression of a Soybean Seed–Specific Lectin Promoter in Transgenic Soybean Embryos*, Dept of Agronomy, Univ of Illinois, Urbana, IL (abstract 140) (1994).
Goossens et al., Co–introduction of an antisense gene for an endogenous seed storage protein can increase expression of a transgene in *Arabidopsis thaliana* seeds, FEBS Letters 456:160–164 (1999).
Liol et al., *Identification of a new arcelin variant in wild been seeds*, Bean Imp Coop,32:28 (1989).
Osborn et al., *Bean arcelin (2) Genetic Variation, inheritance and linkage relationships of a novel seed protein of Phaseolus vulgaris L.*, Theor Appl Genet 71:847–855 (1986).

* cited by examiner

*Primary Examiner*—David T. Fox
*Assistant Examiner*—Georgia Helmer
(74) *Attorney, Agent, or Firm*—Renessen LLC

(57) ABSTRACT

The present invention discloses Arcelin promoters capable of transcribing a heterologous nucleic acid sequence at high levels in plants. The promoters are particularly suited for use in soybean plants and plant cells. Methods of modifying, producing, and using the promoters are also disclosed. The invention further discloses compositions, transformed host cells, transgenic plants, and seeds containing the high-expression Arcelin promoters, and methods for preparing and using the same.

20 Claims, 11 Drawing Sheets

```
                         91                                              150
P-PvArc4-417775-FL   ATTGTTT... .CACCTACAA TGATAATATA TTAAAAAGTG AACTTTAAAT
P-PvArc3-417683-FL   ATTGTTT... .CACCTACAA TGATAATATA TTAAAAAGTG AACTTTAAAT
      P-Pv-Arc5-FL   ATTTTTTTCA CATACAATTA TGATAATATA TTAAAAAGTG AACTTTAAAT
                         391                                             440
P-PvArc4-417775-FL   TAATTTACA. ........... .AGTTAAATT AATTCAGCTT GTCTCCTTGA
P-PvArc3-417683-FL   TAATTTACA. ........... .AGTTAAATT AATTCAGCTT GTCTCCTTGA
      P-Pv-Arc5-FL   TAATTTACAA TATATAGATT CAGTTAAATC AATTCAGCTT GTCTCCTTGA
                         801                                             850
P-PvArc4-417775-FL   TGTTTATGCT CTTTTCGGAA TTAATTAAGT TTTAGTTGTA ATTGTAATAA
P-PvArc3-417683-FL   TGTTTATGCT CTTTTCGGAA TTAATTAAGT TTTAGTTGTA ATTGTAATAA
      P-Pv-Arc5-FL   TGTTT..... .......... .......... .......... .CTGTAATAA
                                                                         950
P-PvArc4-417775-FL   TTAGTCACGA GTGTGTATCC TCACCCCTCA CAAACAACAT TTCAAGAAAA
P-PvArc3-417683-FL   TTAGTCACGA GTGTGTATCC TCACCCCTCA CAAACAACAT TTCAAGAAAA
      P-Pv-Arc5-FL   CTAGTCATGA G......... .CACCACTCA GAGACAAGAT TTCAAGAAAA
                         1351                                            1400
P-PvArc4-417775-FL   ATA....... .....AAATT TTATAAAAAG GGAAAATCAA ATTAGAATTT
P-PvArc3-417683-FL   ATA....... .....AAATT TTATAAAAAG GGAAAATCAA ATTAGAATTT
      P-Pv-Arc5-FL   ATATATAATA TATACAATTA AATAAAAAAG GGAAAATCAA ATTAGAATTT
                         1751                                            1800
P-PvArc4-417775-FL   CGTTGTTTGT TAATTGTTAA TTTTATATTA TTATTTCTCC CTCAAATAAT
P-PvArc3-417683-FL   CGTTGTTTGT TAATTGTTAA TTTTATATTA TTATTTCTCC CTCAAATAAT
      P-Pv-Arc5-FL   CGTTGTTTAA TAATTGTTAA TTTGGAGTT. .......... ...GAATAAT
                         1801                                            1850
P-PvArc4-417775-FL   ATTATAAAAG ATAATGATTC ......GATT TTGCATTTGT TGTTGTATAA
P-PvArc3-417683-FL   ATTATAAAAG ATAATGATTC GATTTGATT TTGCATTTGT TGTTGTATAA
      P-Pv-Arc5-FL   AAAATGAAAG AAAAAAGTTG GA..AAGATT TTGCATTTGT TGTTGTATAA

P-PvArc4-417775-FL   (SEQ ID NO: 10)
P-PvArc3-417683-FL   (SEQ ID NO: 9)
      P-Pv-Arc5-FL   (SEQ ID NO: 11)
```

*Figure 1*

```
!!NA_MULTIPLE_ALIGNMENT 1.0
PileUp of: @/usr4/people/ppdubo/.seqlab-mendel/pileup_1.list Symbol comparison table: GenRunData:pileupdna.cmp  CompCheck: 6876 pileup_1.msf  MSF: 1903  Type: N  July 12, 2000 09:15  Check: 8196 ..

Name: P-PvArc4-417775-FL  Len:  1903  Check: 2130  Weight:  1.00
Name: P-PvArc3-417683-FL  Len:  1903  Check: 8855  Weight:  1.00
Name: P-Pv-Arc5-FL        Len:  1903  Check: 7211  Weight:  1.00

1                                                    50
P-PvArc4-417775-FL   CTGCAGTCCT ACATAATTCT TCTACCGTTA ACCGTCAAAT CATATTTTCA
P-PvArc3-417683-FL   CTGCAGTCCT ACATAATTCT TCTACCGTTA ACCGTCAAAT CATATTTTCA
       P-Pv-Arc5-FL  CTGCAGTCCT ACATAATTCT TCTACAGTTA ACCTTCAAAT CATATTTTCA 51                                                   100
P-PvArc4-417775-FL   TTATTCACAA ATATCTAGTG TCTCATACGA ATAAATATAT ATTGTTT...
P-PvArc3-417683-FL   TTATTCACAA ATATCTAGTA TCTCATACGA ATAAATATAT ATTGTTT...
       P-Pv-Arc5-FL  TTATTCACAA ATATCTAGTC ATTCATACGA ATAAATATAT ATTTTTTCA 101                                                  150
P-PvArc4-417775-FL   .CACCTACAA TGATAATATA TTAAAAAGTG AACTTTAAAT GTAATTTAAT
P-PvArc3-417683-FL   .CACCTACAA TGATAATATA TTAAAAAGTG AACTTTAAAT GTAATTTAAT
       P-Pv-Arc5-FL  CATACAATTA TGATAATATA TTAAAAAGTG AACTTTAAAT TTAATTTAAT 151                                                  200
P-PvArc4-417775-FL   CTCATAAAAT CGACTTATAA AATGAGATTT ATACCTACGA TCGATAAAAA
P-PvArc3-417683-FL   CTCATAAAAT CGACTTATAA AATGAGATTT ATACCTACGA TCGATAAAAA
       P-Pv-Arc5-FL  CTTATAAAAT CAACTTATAA AATGAGATTT CTACCTACGA TTAATAAAAA 201                                                  250
P-PvArc4-417775-FL   TAACTTTAAT ATCATATTAA GAAATAAACT TTAAACCTAA CTCAATTTTA
P-PvArc3-417683-FL   TAACTTTAAT ATCATATTAA GAAATAAACT TTAAACCTAA CTCAATTTTA
       P-Pv-Arc5-FL  TAACTTTGAT ATCATATTAA AAAATAAACT TTAAACCTAA CTCAACTTTA 251                                                  300
P-PvArc4-417775-FL   TAAAACCAAT TTATAAAATA AAATTTACAC TCACTTATAT ATTATAAAAT
P-PvArc3-417683-FL   TAAAACCAAT TTATAAAATA AAATTTACAC TCACTTATAT ATTATAAAAT
       P-Pv-Arc5-FL  TAAAACCAAT TTATAAAATA AAATTTACAC TCAGTTATGA ATTATAAAAT 301                                                  350
P-PvArc4-417775-FL   AAAATAGTTT TTAGGTGACG TGAAATCTCC ATCCGATTAA TCAATATTTT
P-PvArc3-417683-FL   AAAATAGTTT TTAGGTGACG TGAAATCTCC ATCCGATTAA TCAATATTTT
       P-Pv-Arc5-FL  GAAATAGTTT TTAGGTGACG TGGAATCTCC ATCCGATTAA TCAATATTTG
```

*Figure 4a*

```
                        351                                                      400
P-PvArc4-417775-FL      CTGATGTTAT TGTTATTATA GAAACTAAAA ACATGCCAAA TAATTTACA.
P-PvArc3-417683-FL      CTGATGTTAT TGTTATTATA GAAACTAAAA ACATGCCAAA TAATTTACA.
      P-Pv-Arc5-FL      ATGATGTTAT TGTTATTATA GAAACTAAAA ACATGCCAAA TAATTTACAA 401                                                      450
P-PvArc4-417775-FL      .......... .AGTTAAATT AATTCAGCTT GTCTCCTTGA CTAATAAAAC
P-PvArc3-417683-FL      .......... .AGTTAAATT AATTCAGCTT GTCTCCTTGA CTAATAAAAC
      P-Pv-Arc5-FL      TATATAGATT CAGTTAAATC AATTCAGCTT GTCTCCTTGA CTAATAAAAA 451                                                      500
P-PvArc4-417775-FL      ACAACTTTAG ACTATTATTC AGATTTACAC TTCATCTCTC ATGATATCCC
P-PvArc3-417683-FL      ACAACTTTAG ACTATTATTC AGATTTACAC TTCATCTCTC ATGATATCCC
      P-Pv-Arc5-FL      AAAACTTTAG ACTATTATTC AGATTTACAC TTCATCTCTC ATGATATCCC 501                                                      550
P-PvArc4-417775-FL      TCAAAGTGAA TTTCATTCAT GGCACCATTT ATATAATCAA CAATTTTAAA
P-PvArc3-417683-FL      TCAAAGTGAA TTTCATTCAT GGCACCATTT ATATAATCAA CAATTTTAAA
      P-Pv-Arc5-FL      TCAAAGTGAA TTTCATTCAT GGCACCATTT ATATAATCAA CAATTTTAAA 551                                                      600
P-PvArc4-417775-FL      AAGATGCAAA TTTGTACTAG TAAATGCTTC AATGTCCCTG ATAAACACAC
P-PvArc3-417683-FL      AAGATGCAAA TTTGTACTAG TAAATGCTTC AATGTCCCTG ATAAACACAC
      P-Pv-Arc5-FL      AATATGCAAA TTTGTACCAG TAAATGCTTT AATGTCCCTG ATAAACACAA 601                                                      650
P-PvArc4-417775-FL      ACAAAAAAAC CTTTTCATAT TTTTTTCTTA TTAAATAAAG AAATTCATTG
P-PvArc3-417683-FL      ACAAAAAAAC CTTTTCATAT TTTTTTCTTA TTAAATAAAG AAATTCATTG
      P-Pv-Arc5-FL      AAAAAAAAA. .AATTCATAT TTTTTTCTTA TTAAATAAAG AAGTTCATTG 651                                                      700
P-PvArc4-417775-FL      TAAGAGAAAT TAGGATCCTT CAATAGAAAA TGTGTTATTT CCTCATCACC
P-PvArc3-417683-FL      TAAGAGAAAT TAGGATCCTT CAATAGAAAA TGTGTTATTT CCTCATCACC
      P-Pv-Arc5-FL      TAAGAGAAAT TAGGATCCTT CAATAGAAAA TGTGTTATTT CCTCATCACC 701                                                      750
P-PvArc4-417775-FL      AGGAAAAAAA GGACAACAGT TAACACAACA AATTTATGTT TCATTTGAGA
P-PvArc3-417683-FL      AGGAAAAAAA GGACAACAGT TAACACAACA AATTTATGTT TCATTTGAGA
      P-Pv-Arc5-FL      AG..ACAAAG GGCAACAGT TAACAAAACA AATTTATGTT TCATTTGAGA 751                                                      800
P-PvArc4-417775-FL      TTAAGGAAGG TAAGGAAGAA AAAAGATTAA AAAAAATGTC CTTATCTCTT
P-PvArc3-417683-FL      TTAAGGAAGG TAAGGAAGAA AAAAGATTAA AAAAAATGTC CTTATCTCTT
      P-Pv-Arc5-FL      TTAAGGAAGG TAAGGAAGAA AAAAGATTAA AAAAAATGTC CTTATCTCTT
```

*Figure 4b*

```
                      801                                                    850
P-PvArc4-417775-FL    TGTTTATGCT CTTTTCGGAA TTAATTAAGT TTTAGTTGTA ATTGTAATAA
P-PvArc3-417683-FL    TGTTTATGCT CTTTTCGGAA TTAATTAAGT TTTAGTTGTA ATTGTAATAA
    P-Pv-Arc5-FL      TGTTT..... .......... .......... .......... .CTGTAATAA 851                                                    900
P-PvArc4-417775-FL    TAATATAAGA GACTTAAACT TTTAATATAA TAATTATAAT TAGGTTTTTT
P-PvArc3-417683-FL    TAATATAAGA GACTTAAACT TTTAATATAA TAATTATAAT TAGGTTTTTT
    P-Pv-Arc5-FL      TAATATAAGA GACTTAAACT TTTAATATAA TAATTGTAAT TAGG..TTTT 901                                                    950
P-PvArc4-417775-FL    TTAGTCACGA GTGTGTATCC TCACCCCTCA CAAACAACAT TTCAAGAAAA
P-PvArc3-417683-FL    TTAGTCACGA GTGTGTATCC TCACCCCTCA CAAACAACAT TTCAAGAAAA
    P-Pv-Arc5-FL      CTAGTCATGA G......... .CACCACTCA GAGACAAGAT TTCAAGAAAA 951                                                   1000
P-PvArc4-417775-FL    CAATTTTGTT AAACATCTTA TTAGAAACTT TTAGCAAAGT CTTGAAGTTA
P-PvArc3-417683-FL    CAATTTTGTT AAACATCTTA TTAGAAACTT TTAGCAAAGT CTTGAAGTTA
    P-Pv-Arc5-FL      CAATTTTGTT AAACATCTTA TTAGAAACTT TTAGTTAAGT CTTGAAGTTA 1001                                                  1050
P-PvArc4-417775-FL    GAATTAAACA AAAAATTTAC ACACACGAGG AACACAATAA ACCTACTATC
P-PvArc3-417683-FL    GAATTAAACA AAAAATTTAC ACACACGAGG AACACAATAA ACCTACTATC
    P-Pv-Arc5-FL      GAATTAAACA AAAAAAAT.T ACACACGAGA AACACAATAA ACCCACTACC 1051                                                  1100
P-PvArc4-417775-FL    GTCAGGTTAT CATAAGGATG AAATGTTTTG ATACCATTAA ATATAACACA
P-PvArc3-417683-FL    GTCAGGTTAT CATAAGGATG AAATGTTTTG ATACCATTAA ATATAACACA
    P-Pv-Arc5-FL      GTCAGGTTAT CATAAGGATG AAATGTTTTG ATATCATTAA ATATAACACA 1101                                                  1150
P-PvArc4-417775-FL    CACAAAAATA CATGTAATTA TAACAATACA TGTTATAC.. ATATTTTTGA
P-PvArc3-417683-FL    CACAAAAATA CATGTAATTA TAACAATACA TGTTATAC.. ATATTTTTGA
    P-Pv-Arc5-FL      CACAAAAATA CATCTAATTA TAACAATATA TGTTATACAT ATATTTTTGT 1151                                                  1200
P-PvArc4-417775-FL    AAAAACTTAA AGTTTTTCAA AACATTCTTA ATACATGATT AGAGCTTATA
P-PvArc3-417683-FL    AAAAACTTAA AGTTTTTCAA AACATTCTTA ATACATGATT AGAGCTTATA
    P-Pv-Arc5-FL      AAAAACTTAG AGTTTTTCAA AACATTC.TA ATACATGATT AGAGTTTATA 1201                                                  1250
P-PvArc4-417775-FL    GAAATACAAA TATTTAAAAA ATATAACTTT AAAAAAACAT CTTAAAGTC.
P-PvArc3-417683-FL    GAAATACAAA TATTTAAAAA ATATAACTTT AAAAAAACAT CTTAAAGTC.
    P-Pv-Arc5-FL      GAAATACAAA TATTTAAAAA ATATAATTTT AAAAAAACAT TCTAAAGTCA
```

*Figure 4c*

```
                         1251                                                    1300
P-PvArc4-417775-FL       CTCATATCCT CTCACACCGG TGAAATCATT TACTCGTAGT ATAGTACCGT
P-PvArc3-417683-FL       CTCATATCCT CTCACACCGG TGAAATCATT TACTCGTAGT ATAGTACCGT
     P-Pv-Arc5-FL        TTCAGATCCT CTCACACCTG TGTGATCATT TAGTCAT.GT ATGTAGTACA 1301                                                    1350
P-PvArc4-417775-FL       GTCATAATAG TTCACAACAC AGTAAAAAGA ATAAGAATAA ACTAGTGAAT
P-PvArc3-417683-FL       GTCATAATAG TTCACAACAC AGTAAAAAGA ATAAGAATAA ACTAGTGAAT
     P-Pv-Arc5-FL        ATCATTGTAG TTCACAACAG AGTAAAATAA ATAAGGATAA ACTAGGGAAT 1351                                                    1400
P-PvArc4-417775-FL       ATA....... .....AAATT TTATAAAAAG GGAAAATCAA ATTAGAATTT
P-PvArc3-417683-FL       ATA....... .....AAATT TTATAAAAAG GGAAAATCAA ATTAGAATTT
     P-Pv-Arc5-FL        ATATATAATA TATACAATTA AATAAAAAAG GGAAAATCAA ATTAGAATTT 1401                                                    1450
P-PvArc4-417775-FL       TTGATTCCCC ACATAACACA ACTCACCATG CACGCTGCCA CCTCAGCTCC
P-PvArc3-417683-FL       TTGATTCCCC ACATAACACA ACTCACCATG CACGCTGCCA CCTCAGCTCC
     P-Pv-Arc5-FL        TTGATTCCCC ACATGACACA ACTCACCATG CACGCTGCCA CCTCAGCTCC 1451                                                    1500
P-PvArc4-417775-FL       CTCCTCTCCA CACATGTCTC ATGTCACTTT CGACTTTGGC TTTTTCACTA
P-PvArc3-417683-FL       CTCCTCTCCA CACATGTCTC ATGTCACTTT CGACTTTGGC TTTTTCACTA
     P-Pv-Arc5-FL        CTCCTCTCCA CACATGTCTC ATGTCACTTT CGACTTTGGC TTTTTCACTA 1501                                                    1550
P-PvArc4-417775-FL       GGAGACAACT CGCCATGCAC GCTGCCACGT CAGCTCCTTC CTCTTCCCAT
P-PvArc3-417683-FL       GGAGACAACT CGCCATGCAC GCTGCCACGT CAGCTCCTTC CTCTTCCCAT
     P-Pv-Arc5-FL        TGACACAACT CGCCATGCAT GTTGCCACGT GAGCTCCTTC CTCTTCCCAT 1551                                                    1600
P-PvArc4-417775-FL       GATGACACCA CTGGGCATGC ATGATGCCAC CTCAGCTCCC ACCTCTTCTC
P-PvArc3-417683-FL       GATGACACCA CTGGGCATGC ATGATGCCAC CTCAGCTCCC ACCTCTTCTC
     P-Pv-Arc5-FL        GATGACACCA CTGGGCATGC ATGCTGCCAC CTCAGCTCCC ACCTCTTCTC 1601                                                    1650
P-PvArc4-417775-FL       ATTATGAGCC TACTGGCCAT GCACACTGCC ACCTCAGCAC TCCTCTCACT
P-PvArc3-417683-FL       ATTATGAGCC TACTGGCCAT GCACACTGCC ACCTCAGCAC TCCTCTCACT
     P-Pv-Arc5-FL        ATTATGAGCC TACTGGCCAT GCACACTGCC ACCTCAGCAC TCCTCTCACT 1651                                                    1700
P-PvArc4-417775-FL       TCCCATTGCT ACCTGCCAAA CCGCTTCTCT CTATAAATAT CTCTTTAAAT
P-PvArc3-417683-FL       TCCCATTGCT ACCTGCCAAA CCGCTTCTCT CTATAAATAT CTCTTTAAAT
     P-Pv-Arc5-FL        TCCCATTGCT ACCTGCCAAA CCGCTTCTCT CCATAAATAT CTATTTAAAT
```

*Figure 4d*

```
                    1701                                                    1750
P-PvArc4-417775-FL  TTAAACTAAT TATTTCATAT ACTTTTTTGA TGACGTGGAT GCATTGCCAT
P-PvArc3-417683-FL  TTAAACTAAT TATTTCATAT ACTTTTTTGA TGACGTGGAT GCATTGCCAT
      P-Pv-Arc5-FL  TTAAACTAAT TATTTCATAT ACTTTTTTGA TGACGTGGAT GCATTGCCAT 1751                                                    1800
P-PvArc4-417775-FL  CGTTGTTTGT TAATTGTTAA TTTTATATTA TTATTTCTCC CTCAAATAAT
P-PvArc3-417683-FL  CGTTGTTTGT TAATTGTTAA TTTTATATTA TTATTTCTCC CTCAAATAAT
      P-Pv-Arc5-FL  CGTTGTTTAA TAATTGTTAA TTTGGAGTT. .......... ...GAATAAT 1801                                                    1850
P-PvArc4-417775-FL  ATTATAAAAG ATAATGATTC ......GATT TTGCATTTGT TGTTGTATAA
P-PvArc3-417683-FL  ATTATAAAAG ATAATGATTC GATTTTGATT TTGCATTTGT TGTTGTATAA
      P-Pv-Arc5-FL  AAAATGAAAG AAAAAAGTTG GA..AAGATT TTGCATTTGT TGTTGTATAA 1851                                                    1900
P-PvArc4-417775-FL  ATAGAGAAGA GAGTGATGGT TAATGCATGA ATGCATGATC AGATCTGCCA
P-PvArc3-417683-FL  ATAGAGAAGA GAGTGATGGT TAATGCATGA ATGCATGATC AGATCTGCCA
      P-Pv-Arc5-FL  ATAGAGAAGA GAGTGATGGT TAATGCATGA ATGCATGATC AGATCTGCCA

1901
P-PvArc4-417775-FL  TGG (SEQ ID NO: 13)
P-PvArc3-417683-FL  TGG (SEQ ID NO: 12)
      P-Pv-Arc5-FL  TGG (SEQ ID NO: 14)
```

*Figure 4e*

| Plasmid | Promoter | 5' UTR | Coding sequence | 3' terminator |
|---|---|---|---|---|
| pMON55534 | tARC5 | ARC5 | GUS | ADR12 |
| pMON55535 | tARC5 | ARC5 | GUS | E9 |
| pMON55540 | tARC5 | GmHSP17.9 | GUS | E9 |
| pMON55569 | tARC5 | GmdSSU | GUS | E9 |
| pMON55570 | tARC5 | PetHSP70 | GUS | E9 |
| pMON55575 | tARC5 | ARC5 | GUS | Arc5 |

Figure 5

ARCELIN-5 PROMOTER AND USES THEREOF

CROSS REFERENCE TO RELATED APPLICATION

This application claims priority to U.S. Provisional Application Ser. No. 60/255,879, filed Dec. 18, 2000, and having the title "Arecelin 5 Promoter and Uses Thereof", which is herein incorporated by reference in its entirety.

FIELD OF THE INVENTION

The present invention generally relates to the field of plant genetics. More specifically, the present invention relates to gene expression in plants. The invention provides promoters capable of transcribing a heterologous nucleic acid sequence at a high level in plants, and methods of modifying, producing, and using the same. The invention also provides transformed host cells, transgenic plants, and seeds containing the high-expression promoters, and methods for preparing and using the same.

BACKGROUND OF THE INVENTION

Plants and seeds provide an important source of dietary protein for humans and livestock. However, the protein content of plants and seeds is often incomplete. For example, many plant and seed proteins are deficient in one or more essential amino acids. This deficiency may be overcome by genetically enhancing the native proteins to have a more nutritionally complete composition of amino acids (or some other desirable feature). Alternatively, a non-native (or heterologous) protein exhibiting a desirable characteristic may be introduced into the plant or seed. These approaches are useful in producing proteins exhibiting important agricultural (e.g., insecticidal), nutritional, and pharmaceutical properties.

Despite the availability of many molecular tools, the genetic modification of plants and seeds is often constrained by an insufficient accumulation of the engineered protein. Many intracellular processes may impact the overall protein accumulation, including transcription, translation, protein assembly and folding, methylation, phosphorylation, transport, and proteolysis. Intervention in one or more of these processes can increase the amount of protein produced in genetically engineered plants and seeds.

For example, raising the steady-state level of mRNA in the cytosol often yields an increased accumulation of translated protein. Many factors may contribute to increasing the steady-state level of an mRNA in the cytosol, including the rate of transcription controlled by promoter strength and other regulatory features, efficiency of mRNA processing, and the overall stability of the mRNA.

Among these factors, the promoter portion of a gene plays a central role. Along the promoter region, the transcription machinery is assembled and transcription is initiated. This early step is often rate-limiting relative to subsequent stages of protein production. Transcription initiation at the promoter may be regulated in several ways. For example, a promoter may be induced by the presence of a particular compound, express a gene only in a specific tissue, or constitutively express a coding sequence. Thus, transcription of a coding sequence may be modified by operably linking the coding sequence to promoters with different regulatory characteristics.

The promoters derived from the genes of seed storage proteins often exhibit high levels of expression. For example, seeds of *Phaseolus vulgaris* typically contain large amounts of phaseolin (36–46%, w/w), globulin-2 (5–12%), albumin (12–16%), and prolamine (2–4%). Thus, the promoters derived from such genes may be useful in expressing high levels of heterologous structural nucleic acid sequences.

However, the transcriptional activity of even these strong promoters may vary from one plant context to the next. For example, a number of promoters have exhibited strong activity in tobacco, petunia, and *Arabidopsis*, relative to the expression levels generated in these plants by the 7Sα' promoter. However, none of these promoters have been reported to demonstrate comparable activity in transgenic soybean plants. Thus, a promoter which functions in one plant species or cultivar may not function at a similar level or manner in a different plant species or cultivar.

Romero et al. reported a new seed protein in *P. vulgaris* collected at Arcelia, Mexico (from accession PI 325690; CIAT No. 12882B). Accordingly, the protein was named Arcelin (Andreas et al., 1986; Osborn et al., 1986). Several Arcelin variants have been subsequently reported (e.g., Arcelin-3 from accession PI 417683 (CIAT No. G12922); Arcelin-4 from accession PI 417775 (CIAT No. G12949)). One such variant, designated Arcelin-5, was reported by Lioi, et al (Lioi and Bollini, 1989). The cDNA of Arcelin-5 was described by Goossens, et al. (Goossens et al., 1994).

A genomic clone of Arcelin-5, including an undefined 5' and 3' region was reportedly expressed in transgenic plants. This undefined region included about 1.8 kb base pairs 5' to the Arcelin-5 coding region. Expression was reported in *Arabidopsis* and *Phaseolus acutifolius* (Goossens et al., 1999). However, the expression was lower than that found in the wild-type *P. vulgaris* from which Arcelin-5 was originally identified. Therefore, the genetic background is important in modulating Arcelin-5 expression. Also, since the whole genomic clone of Arcelin-5 was used by Goossens, the relative strength of the Arcelin-5 promoter was not clear. Thus although expression of an Arcelin species was reported, the effectiveness of such Arcelin promoters in crops such as maize and soybean remain totally unknown. Consequently, there is a need in the art for promoters capable of generating relatively high levels of transcription in important crop species, such as maize and soybean.

SUMMARY OF THE INVENTION

The present invention provides promoters capable of transcribing a heterologous structural nucleic acid sequence at a high level in plants, and methods of modifying, producing, and using the same. The invention also provides compositions, transformed host cells, transgenic plants, and seeds containing the high-expression promoters, and methods for preparing and using the same.

The present invention includes and provides a transformed soybean plant cell containing a nucleic acid molecule that comprises in the 5' to 3' direction: a promoter having a nucleic acid sequence that is at least 94% identical to SEQ ID NO: 1; operably linked to a structural nucleic acid sequence; wherein the promoter is heterologous with respect to the structural nucleic acid sequence.

The present invention includes and provides a transgenic soybean plant containing a nucleic acid molecule that comprises in the 5' to 3' direction: a promoter having a nucleic acid sequence that: is at least 94% identical to SEQ ID NO: 1; operably linked to a structural nucleic acid sequence; wherein the promoter is heterologous with respect to the structural nucleic acid sequence.

The present invention includes and provides a transformed soybean plant cell containing a nucleic acid molecule that comprises, in the 5' to 3' direction, a promoter operably linked to a heterologous structural nucleic acid sequence. The promoter preferably hybridizes under stringent conditions with SEQ ID NO: 1, or the complement thereof; or is at least 94% identical to SEQ ID NO: 1.

The present invention includes and provides a transgenic soybean plant containing a nucleic acid molecule that comprises, in the 5' to 3' direction, a promoter operably linked to a heterologous structural nucleic acid sequence. The promoter preferably hybridizes under stringent conditions with SEQ ID NO: 1, or the complement thereof; or is at least 94% identical to SEQ ID NO: 1.

The present invention includes and provides a transformed plant cell containing a nucleic acid molecule that comprises, in the 5' to 3' direction, a promoter operably linked to a heterologous structural nucleic acid sequence. The promoter preferably hybridizes under stringent conditions with SEQ ID NO: 1, or the complement thereof; or is at least 94% identical to SEQ ID NO: 1.

The present invention includes and provides a transgenic plant containing a nucleic acid molecule that comprises, in the 5' to 3' direction, a promoter operably linked to a heterologous structural nucleic acid sequence. The promoter preferably hybridizes under stringent conditions with SEQ ID NO: 1, or the complement thereof; or is at least 94% identical to SEQ ID NO: 1.

The present invention includes and provides a method of transforming a plant cell. The method generally comprises providing a nucleic acid molecule that comprises, in the 5' to 3' direction, a promoter operably linked to a heterologous structural nucleic acid sequence; and transforming a plant cell with the nucleic acid molecule. The promoter preferably hybridizes under stringent conditions with SEQ ID NO: 1, or the complement thereof; or is at least 94% identical to SEQ ID NO: 1.

The present invention includes and provides a method of producing a transgenic plant. The method generally comprises providing a nucleic acid molecule that comprises, in the 5' to 3' direction, a promoter operably linked to a heterologous structural nucleic acid sequence; transforming a plant cell with the nucleic acid molecule; and culturing the transformed plant cell under conditions effective to produce a plant. The promoter preferably hybridizes under stringent conditions with SEQ ID NO: 1, or the complement thereof; or is at least 94% identical to SEQ ID NO: 1.

BRIEF DESCRIPTION OF THE SEQUENCES

SEQ ID NO: 1 is a truncated *P. vulgaris* exotic genotype G02771 Arcelin-5 promoter sequence.
SEQ ID NO: 2 is a truncated *P. vulgaris* exotic genotype G02771 Arcelin-5 promoter sequence.
SEQ ID NO: 3 is a GmHSP17.9 5' UTR sequence.
SEQ ID NO: 4 is a PetHSP70 5' UTR sequence.
SEQ ID NO: 5 is a GmdSSU 5' UTR sequence.
SEQ ID NO: 6 is an ADR12 3' terminator sequence.
SEQ ID NO: 7 is an E9 3' terminator sequence.
SEQ ID NO: 8 is an Arc5 3' terminator sequence.
SEQ ID NO: 9 is an Arcelin-3 promoter sequence as shown in FIG. 1.
SEQ ID NO: 10 is an Arcelin-4 promoter sequence as shown in FIG. 1.
SEQ ID NO: 11 is an Arcelin-5 promoter sequence as shown in FIG. 1.
SEQ ID NO: 12 is an Arcelin-3 promoter sequence as shown in FIGS. 4a–e.
SEQ ID NO: 13 is an Arcelin-4 promoter sequence as shown in FIG. 4a–e.
SEQ ID NO: 14 is an Arcelin-5 promoter sequence as shown in FIG. 4a–e.

BRIEF DESCRIPTION OF THE FIGURES

FIG. 1 is a sequence alignment of partial Arcelin-3, Arcelin-4, and Arcelin-5 promoter nucleic acid sequences. Differences between the sequences are noted.

FIGS. 4a, 4b, 4c, 4d, and 4e represent a sequence alignment of full length Arcelin-3, Arcelin-4, and Arcelin-5 promoter nucleic acid sequences.

FIG. 5 is a table showing various constructs having an Arcelin-5 promoter sequence.

DEFINITIONS

Figure 2:
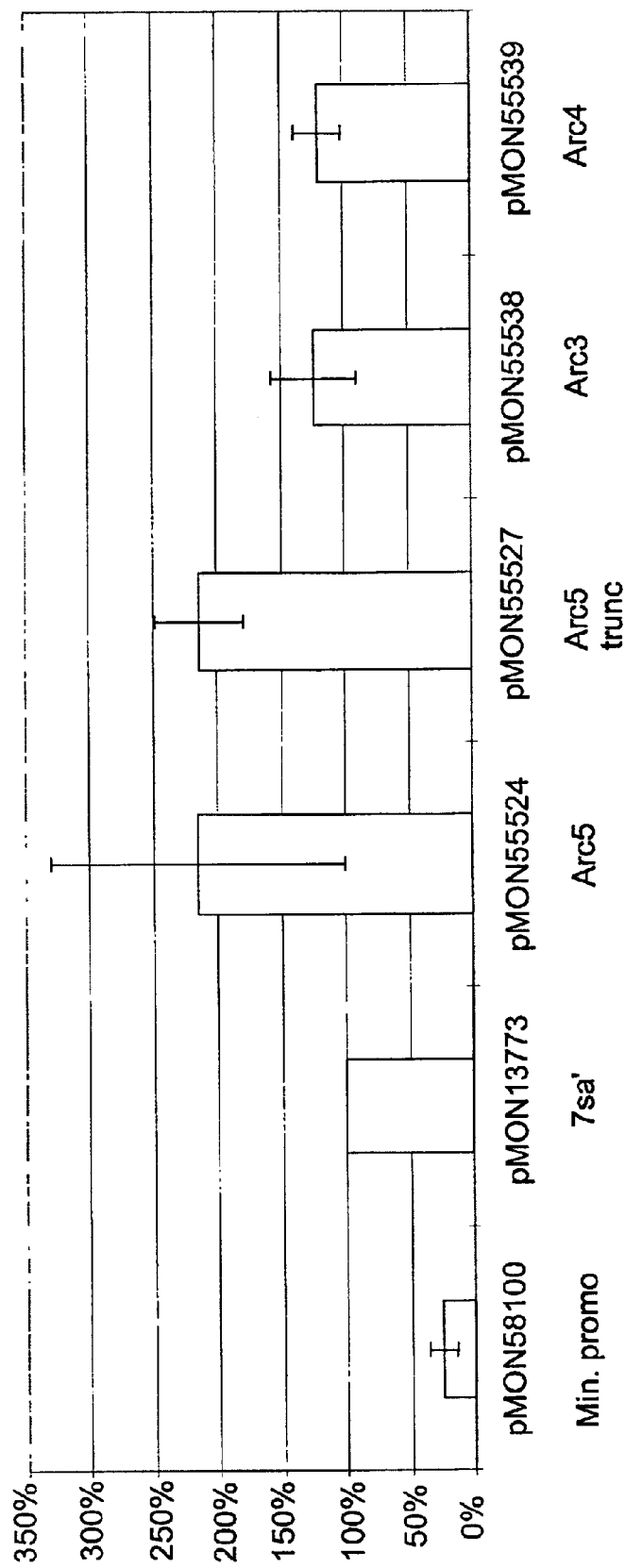
FIG. 2 compares the promoter activities of various Arcelin-3, Arcelin-4, and Arcelin-5 promoters in transiently transformed soybean tissue.

The following definitions are provided as an aid to understanding the detailed description of the present invention.

The term "Arcelin-5 promoter" refers to a promoter region derived from or constructed based upon a region 5'to the transcription start site of the Arcelin-5 coding sequence. The Arcelin-5 promoter is further defined as not being an Arcelin-1, (Osborn, et al. Science, 240:207–210, 1988), -2 (John, et al., Gene 86:171–176, 1990), -3, or -4 (Mirkov, et al., Plant Mol. Biol., 26:1103–1113, 1994) promoter.

The phrases "coding sequence," "structural sequence," and "structural nucleic acid sequence" refer to a physical structure comprising an orderly arrangement of nucleic acids. The nucleic acids are arranged in a series of nucleic acid triplets that each form a codon. Each codon encodes for a specific amino acid. Thus the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The phrases "DNA sequence" and "nucleic acid sequence" refer to a physical structure comprising an orderly arrangement of nucleic acids. The DNA sequence or nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The term "expression of antisense RNA" refers to the transcription of a DNA to produce a first RNA molecule capable of hybridizing to a second RNA molecule. Formation of the RNA—RNA hybrid inhibits translation of the second RNA molecule to produce a gene product.

The term "gene" refers to chromosomal DNA, plasmid DNA, cDNA, synthetic DNA, or other DNA that encodes a peptide, polypeptide, protein, or RNA molecule.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

The phrase "heterologous" refers to the relationship between two or more nucleic acid or protein sequences that are derived from different sources. For example, a promoter is heterologous with respect to a coding sequence if such a combination is not normally found in Nature. In addition, a particular sequence may be "heterologous" with respect to a cell or organism into which it is inserted (i.e. does not naturally occur in that particular cell or organism).

"Hybridization" refers to the ability of a strand of nucleic acid to join with a complementary strand via base pairing. Hybridization occurs when complementary nucleic acid sequences in the two nucleic acid strands contact one another under appropriate conditions.

The phrase "operably linked" refers to the functional spatial arrangement of two or more nucleic acid regions or nucleic acid sequences. For example, a promoter region may be positioned relative to a nucleic acid sequence such that transcription of the nucleic acid sequence is directed by the promoter region. Thus, the promoter region is "operably linked" to the nucleic acid sequence.

The term "promoter" or "promoter region" refers to a nucleic acid sequence, usually found upstream (5') to a coding sequence, that directs transcription of the nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The term "recombinant vector" refers to any agent such as a plasmid, cosmid, virus, autonomously replicating sequence, phage, or linear or circular single-stranded or double-stranded DNA or RNA nucleotide sequence. The recombinant vector may be derived from any source; is capable of genomic integration or autonomous replication; and comprises a promoter nucleic acid sequence operably linked to one or more nucleic acid sequences. A recombinant vector is typically used to introduce such operably linked sequences into a suitable host.

"Regulatory sequence" refers to a nucleotide sequence located upstream (5'), within, or downstream (3') to a coding sequence. Transcription and expression of the coding sequence is typically impacted by the presence or absence of the regulatory sequence.

The term "substantially homologous" refers to two sequences which are at least 90% identical in sequence, as measured by the BestFit program described herein (Version 10; Genetics Computer Group, Inc., University of Wisconsin Biotechnology Center, Madison, Wis.), using default parameters.

The term "transformation" refers to the introduction of nucleic acid into a recipient host. The term "host" refers to bacteria cells, fungi, animals and animal cells, plants and plant cells, or any plant parts or tissues including protoplasts, calli, roots, tubers, seeds, stems, leaves, seedlings, embryos, and pollen.

DETAILED DESCRIPTION OF THE PREFERRED EMBODIMENTS

The present invention provides promoters capable of transcribing a heterologous structural nucleic acid sequence at a high level in plants, and methods of modifying, producing, and using the same. The invention also provides compositions, transformed host cells, transgenic plants, and seeds containing the high-expression promoters, and methods for preparing and using the same.

Promoters

The present invention provides a promoter having a nucleic acid sequence that hybridizes to SEQ ID NO: 1, the complement thereof, or any fragments thereof. The present invention also provides a promoter having a nucleic acid sequence of SEQ ID NO: 1, the complement thereof, or any fragments thereof.

The present invention provides a promoter having a nucleic acid sequence that hybridizes to SEQ ID NO: 2, the complement thereof, or any fragments thereof. The present invention also provides a promoter having a nucleic acid sequence of SEQ ID NO: 2, the complement thereof, or any fragments thereof.

The present invention provides a promoter having a nucleic acid sequence that hybridizes to SEQ ID NO: 14, the complement thereof, or any fragments thereof. The present invention also provides a promoter having a nucleic acid sequence of SEQ ID NO: 14, the complement thereof, or any fragments thereof.

Nucleic acid hybridization is a technique well known to those of skill in the art of DNA manipulation. The hybridization properties of a given pair of nucleic acids is an indication of their similarity or identity.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C.

High stringency conditions may be used to select for nucleic acid sequences with higher degrees of identity to the disclosed nucleic acid sequences (Sambrook et al., 1989).

The high stringency conditions typically involve nucleic acid hybridization in about 2× to about 10× SSC (diluted from a 20× SSC stock solution containing 3 M sodium chloride and 0.3 M sodium citrate, pH 7.0 in distilled water), about 2.5× to about 5× Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. The high stringency conditions are preferably provided by 6× SSC, 5× Denhardt's solution, 100 mg/mL fish sperm DNA, and 0.1% (w/v) SDS, with an incubation at 55° C. for several hours.

The hybridization is generally followed by several wash steps. The wash compositions generally comprise 0.5× to about 10× SSC, and 0.01% (w/v) to about 0.5% (w/v) SDS with a 15 minute incubation at about 20° C. to about 70° C. Preferably, the nucleic acid segments remain hybridized after washing at least one time in 0.1× SSC at 65° C.

The nucleic acid sequence of the promoter preferably hybridizes, under low or high stringency conditions, with SEQ ID NO: 1, the complement thereof, or any fragments thereof. The promoter most preferably hybridizes under high stringency conditions with SEQ ID NO: 1, the complement thereof, or any fragments thereof.

In an alternative embodiment, the promoter comprises a nucleic acid sequence that is at least 85% identical, and more preferably at least 86, 87, 88, 89, 90, 91, 92, 93, 94, 95, 96, 97, 98, or 99% identical to SEQ ID NO: 1. The promoter most preferably comprises or is SEQ ID NO: 1.

The nucleic acid sequence of the promoter preferably hybridizes, under low or high stringency conditions, with SEQ ID NO: 2, the complement thereof, or any fragments thereof. The promoter most preferably hybridizes under high stringency conditions with SEQ ID NO: 2, the complement thereof, or any fragments thereof.

In an alternative embodiment, the promoter comprises a nucleic acid sequence that is at least 85% identical, and more preferably at least 86, 87, 88, 89, 90, 91, 92, 93, 94, 95, 96, 97, 98, or 99% identical to SEQ ID NO: 2. The promoter most preferably comprises or is SEQ ID NO: 2.

The nucleic acid sequence of the promoter preferably hybridizes, under low or high stringency conditions, with SEQ ID NO: 14, the complement thereof, or any fragments thereof. The promoter most preferably hybridizes under high stringency conditions with SEQ ID NO: 14, the complement thereof, or any fragments thereof.

In an alternative embodiment, the promoter comprises a nucleic acid sequence that is at least 85% identical, and more preferably at least 86, 87, 88, 89, 90, 91, 92, 93, 94, 95, 96, 97, 98, or 99% identical to SEQ ID NO: 14. The promoter most preferably comprises or is SEQ ID NO: 14.

The percent of sequence identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, 1981; Smith, et al., 1983). The percent identity is most preferably determined using the "Best Fit" program.

The present invention also provides nucleic acid molecule fragments of SEQ ID NO: 1, fragments of nucleic acid molecules that hybridize it nucleic acid molecules having SEQ ID NO: 1, fragments of nucleic acid molecules that exhibit sequence identity with SEQ ID NO: 1, and complements of any of these molecules.

The present invention also provides nucleic acid molecule fragments of SEQ ID NO: 2, fragments of nucleic acid molecules that hybridize it nucleic acid molecules having SEQ ID NO: 2, fragments of nucleic acid molecules that exhibit sequence identity with SEQ ID NO: 2, and complements of any of these molecules.

The present invention also provides nucleic acid molecule fragments of SEQ ID NO: 14, fragments of nucleic acid molecules that hybridize it nucleic acid molecules having SEQ ID NO: 14, fragments of nucleic acid molecules that exhibit sequence identity with SEQ ID NO: 14, and complements of any of these molecules.

In an alternative embodiment, the fragments are between 250 and 15 nucleotides, more preferably between 150 and 15 nucleotides, even more preferably between 100 and 15 nucleotides, 50 and 15 nucleotides or 25 and 15 nucleotides long. In another preferred embodiment, the fragments are between 250 and 50 nucleotides, more preferably between 150 and 15 nucleotides, even more preferably between 100 and 50 nucleotides, 50 and 25 nucleotides or 25 and 20 nucleotides long. In another alternative embodiment, the fragments are between 250 and 100 nucleotides, more preferably between 150 and 100 nucleotides, even more preferably between 100 and 75 nucleotides long.

Promoter Activity

The activity or strength of a promoter may be measured in terms of the amount of RNA or protein accumulation it specifically produces, relative to the total amount of cellular RNA or protein. The promoter preferably expresses an operably linked nucleic acid sequence at a level greater than 2.5%; more preferably greater than 5, 6, 7, 8, or 9%; even more preferably greater than 10, 11, 12, 13, 14, 15, 16, 17, 18, or 19%; and most preferably greater than 20% of the total cellular RNA or protein.

Alternatively, the activity or strength of a promoter may be expressed relative to a well-characterized promoter (for which transcriptional activity was previously assessed). For example, a less-characterized promoter may be operably linked to a reporter sequence (e.g., GUS) and introduced into a specific cell type. A well-characterized promoter (e.g. the 7Sα' promoter) is similarly prepared and introduced into the same cellular context. Transcriptional activity of the unknown promoter is determined by comparing the amount of reporter expression, relative to the well characterized promoter. The activity of the presently disclosed promoter is preferably as strong as the 7Sα' promoter when compared in the same cellular context. The cellular context is preferably canola, soybean, or maize; and most preferably is soybean.

Structural Nucleic Acid Sequences

The promoter of the present invention may be operably linked to a structural nucleic acid sequence that is heterologous with respect to the promoter. The structural nucleic acid sequence may generally be any nucleic acid sequence for which an increased level of transcription is desired. The structural nucleic acid sequence preferably encodes a polypeptide that is suitable for incorporation into the diet of a human or an animal. Suitable structural nucleic acid sequences include those encoding seed storage proteins, herbicide resistance proteins, disease resistance proteins, fatty acid biosynthetic enzymes, tocopherol biosynthetic enzymes, amino acid biosynthetic enzymes, or insecticidal proteins. Preferred structural nucleic acid sequences include, but are not limited to, gamma methyltransferase, phytyl prenyltransferase, beta-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7Sα' seed storage protein, 11S seed storage protein, glycinin, beta-conglycinin, phaseolin, maize globulin-1, maize zeins, seed albumin, and seed lectin.

Alternatively, the promoter and structural nucleic acid sequence may be designed to down-regulate a specific nucleic acid sequence. This is typically accomplished by linking the promoter to a structural nucleic acid sequence that is oriented in the antisense direction. One of ordinary skill in the art is familiar with such antisense technology. Briefly, as the antisense nucleic acid sequence is transcribed, it hybridizes to and sequesters a complimentary nucleic acid sequence inside the cell. This duplex RNA molecule cannot be translated into a protein by the cell's translational machinery. Thus, the cellular complimentary sequence is effectively down regulated as the subsequent steps of translation are disrupted.

Any nucleic acid sequence may be negatively regulated in this manner. Targets of such regulation may include polypeptides that have a low content of essential amino acids, yet are expressed at a relatively high level in a particular tissue. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived feed.

Modified Structural Nucleic Acid Sequences

The promoter of the present invention may also be operably linked to a modified structural nucleic acid sequence that is heterologous with respect to the promoter. The structural nucleic acid sequence may be modified to provide various desirable features. For example, a structural nucleic acid sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

In a preferred embodiment, the structural nucleic acid sequence is enhanced to encode a polypeptide having an increased content of at least one, and more preferably 2, 3, or 4 of the essential amino acids selected from the group consisting of histidine, lysine, methionine, and phenylalanine. Non-essential amino acids may also be added, as needed, for structural and nutritive enhancement of the polypeptide. Structural nucleic acid sequences particularly suited to such enhancements include those encoding native polypeptides that are expressed at relatively high levels, have a particularly low content of essential amino acids, or both. An example of such are the seed storage proteins, such as glycinin and β-conglycinin. Other suitable targets include phaseolin, lectin, zeins, and albumin.

In an alternative embodiment, the structural nucleic acid sequence is modified to encode a polypeptide having improved rumen resistance, increased resistance to proteolytic degradation, or both improved rumen resistance and increased resistance to proteolytic degradation, relative to the unmodified structural nucleic acid sequence from which it is engineered. The modified structural nucleic acid sequence may generally encode any polypeptide that is suitable for incorporation into the diet of an animal. The modified structural nucleic acid sequence preferably encodes a polypeptide that is expressed at relatively high concentrations in a given plant tissue, such as a seed storage protein.

Codon Usage in Structural Nucleic Acid Sequences

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Other Modifications of Structural Nucleic Acid Sequences

Additional variations in the structural nucleic acid sequences described above may encode proteins having equivalent or superior characteristics when compared to the proteins from which they are engineered. Mutations may include deletions, insertions, truncations, substitutions, fusions, shuffling of motif sequences, and the like.

Mutations to a structural nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a structural nucleic acid sequence. Examples include single strand rescue (Kunkel, et al., 1985), unique site elimination (Deng and Nickloff, 1992), nick protection (Vandeyar, et al., 1988), and PCR (Costa, et al., 1996). Random or non-specific mutations may be generated by chemical agents (for a general review, see Singer and Kusmierek, 1982) such as nitrosoguanidine (Cerda-Olmedo et al., 1968; Guerola, et al., 1971) and 2-aminopurine (Rogan and Bessman, 1970); or by biological methods such as passage through mutator strains (Greener, et al., 1997).

The modifications may result in either conservative or non-conservative changes in the amino acid sequence. Conservative changes result from additions, deletions, substitutions, etc. in the structural nucleic acid sequence which do not alter the final amino acid sequence of the protein. In a preferred embodiment, the protein has between 0 and 500 conservative changes, more preferably between 0 and 300 conservative changes, even more preferably between 0 and 150 conservative changes, and most preferably between 0 and 75 conservative changes.

Non-conservative changes include additions, deletions, and substitutions which result in an altered amino acid sequence. In a preferred embodiment, the protein has between 0 and 250 non-conservative amino acid changes, more preferably between 0 and 100 non-conservative amino acid changes, even more preferably between 0 and 50 non-conservative amino acid changes, and most preferably between 0 and 30 non-conservative amino acid changes.

Additional methods of making the alterations described above are described by Ausubel et al. (1995); Bauer et al. (1985); Craik (1985); Frits Eckstein et al. (1982); Sambrook et al. (1989); Smith et al. (1981); and Osuna et al. (1994).

Modifications may be made to the protein sequences of the present invention and the nucleic acid segments which encode them that maintain the desired properties of the molecule. The following is a discussion based upon changing the amino acid sequence of a protein to create an equivalent, or possibly an improved, second-generation molecule. The amino acid changes may be achieved by changing the codons of the structural nucleic acid sequence, according to the codons given in Table 1.

TABLE 1

Codon degeneracy of amino acids

| Amino Acid | One Letter | Three Letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |

TABLE 1-continued

Codon degeneracy of amino acids

| Amino Acid | One Letter | Three Letter | Codons |
|---|---|---|---|
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of the desired activity. It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted proteins having improved rumen resistance, increased resistance to proteolytic degradation, or both improved rumen resistance and increased resistance to proteolytic degradation, relative to the unmodified polypeptide from which they are engineered.

Recombinant Vectors

Any of the promoters and structural nucleic acid sequences described above may be provided in a recombinant vector. A recombinant vector typically comprises, in a 5' to 3' orientation: a promoter to direct the transcription of a structural nucleic acid sequence and a structural nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

Means for preparing recombinant vectors are well known in the art. Methods for making recombinant vectors particularly suited to plant transformation are described in U.S. Pat. Nos. 4,971,908, 4,940,835, 4,769,061 and 4,757,011. These type of vectors have also been reviewed (Rodriguez, et al., 1988; Glick, et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985).

Promoters in the Recombinant Vectors

The promoter used in the recombinant vector preferably transcribes a heterologous structural nucleic acid sequence at a high level in a plant. More preferably, the promoter hybridizes to SEQ ID NO: 1, the complement thereof, or any fragments thereof. Suitable hybridization conditions are described above. The nucleic acid sequence of the promoter preferably hybridizes, under low or high stringency conditions, with SEQ ID NO: 1, the complement thereof, or any fragments thereof. The promoter most preferably hybridizes under high stringency conditions with SEQ ID NO: 1, the complement thereof, or any fragments thereof.

In an alternative embodiment, the promoter comprises a nucleic acid sequence that is at least 85% identical, and more preferably at least 86, 87, 88, 89, 90, 91, 92, 93, 94, 95, 96, 97, 98, or 99% identical to SEQ ID NO: 1. The promoter most preferably comprises or is SEQ ID NO: 1. Preferred methods for calculating the percent identity of two or more nucleic acid sequences is described above. In another alternative embodiment, the promoter is a fragment as described above.

In another embodiment, the promoter hybridizes to SEQ ID NO: 2, the complement thereof, or any fragments thereof. Suitable hybridization conditions are described above. The nucleic acid sequence of the promoter preferably hybridizes, under low or high stringency conditions, with SEQ ID NO: 2, the complement thereof, or any fragments thereof. The promoter most preferably hybridizes under high stringency conditions with SEQ ID NO: 2, the complement thereof, or any fragments thereof.

In an alternative embodiment, the promoter comprises a nucleic acid sequence that is at least 85% identical, and more preferably at least 86, 87, 88, 89, 90, 91, 92, 93, 94, 95, 96, 97, 98, or 99% identical to SEQ ID NO: 2. The promoter most preferably comprises or is SEQ ID NO: 2. Preferred methods for calculating the percent identity of two or more nucleic acid sequences is described above. In another alternative embodiment, the promoter is a fragment as described above.

In another embodiment, the promoter hybridizes to SEQ ID NO: 14, the complement thereof, or any fragments thereof. Suitable hybridization conditions are described above. The nucleic acid sequence of the promoter preferably hybridizes, under low or high stringency conditions, with SEQ ID NO: 14, the complement thereof, or any fragments thereof. The promoter most preferably hybridizes under high stringency conditions with SEQ ID NO: 14, the complement thereof, or any fragments thereof.

In an alternative embodiment, the promoter comprises a nucleic acid sequence that is at least 85% identical, and more preferably at least 86, 87, 88, 89, 90, 91, 92, 93, 94, 95, 96, 97, 98, or 99% identical to SEQ ID NO: 14. The promoter most preferably comprises or is SEQ ID NO: 14. Preferred methods for calculating the percent identity of two or more nucleic acid sequences is described above. In another alternative embodiment, the promoter is a fragment as described above.

Additional Promoters in the Recombinant Vector

One or more additional promoters may also be provided in the recombinant vector. These promoters may be operably linked to any of the structural nucleic acid sequences described above. Alternatively, the promoters may be operably linked to other nucleic acid sequences, such as those encoding transit peptides, selectable marker proteins, or antisense sequences.

These additional promoters may be selected on the basis of the cell type into which the vector will be inserted. Promoters which function in bacteria, yeast, and plants are all well taught in the art. The additional promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described (Poszkowski, et al., 1989; Odell, et al., 1985; Chau, et al., 1989).

Often-used constitutive promoters include the CaMV 35S promoter (Odell, J. T. et al., 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams, S. W. et al, 1992), induced by application of safeners (substituted benzenesulfonamide herbicides; Hershey, H. P. and Stoner, T. D., 1991), heat-shock promoters (Ou-Lee et al., 1986; Ainley et al., 1990), a nitrate-inducible promoter derived from the spinach nitrite reductase structural nucleic acid sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemeier et al., 1989; Feinbaum, R. L. et al., 1991; Weisshaar, B. et al., 1991; Lam, E. and Chua, N. H., 1990; Castresana, C. et al., 1988; Schulze-Lefert et al., 1989).

Examples of useful tissue-specific, developmentally-regulated promoters include the β-conglycinin 7Sα' promoter (Doyle, J. J. et al., 1986; Slighton and Beachy, 1987), and seed-specific promoters (Knutzon, D. S. et al., 1992; Bustos, M. M. et al., 1991; Lam and Chua, 1991; Stayton et al., 1991). Plant functional promoters useful for preferential expression in seed plastid include those from plant storage proteins and from proteins involved in fatty acid biosynthesis in oilseeds. Examples of such promoters include the 5' regulatory regions from such structural nucleic acid sequences as napin (Kridl et al., 1991), phaseolin, zein, soybean trypsin inhibitor, ACP, stearoyl-ACP desaturase, and oleosin. Seed-specific regulation is discussed in EP 0 255 378.

Another exemplary tissue-specific promoter is the lectin promoter, which is specific for seed tissue. The Lectin protein in soybean seeds is encoded by a single structural nucleic acid sequence (Le1) that is only expressed during seed maturation and accounts for about 2 to about 5% of total seed mRNA. The lectin structural nucleic acid sequence and seed-specific promoter have been fully characterized and used to direct seed specific expression in transgenic tobacco plants (Vodkin et al., 1983; Lindstrom et al., 1990.)

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens;* the cauliflower mosaic virus *(CaMV)* 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBlSCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from *Arabidopsis* (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); Potato patatin (Wenzler et al., 1989); the ubiquitin promoter from maize (Christensen et al., 1992); and the actin promoter from rice (McElroy et al., 1990).

The additional promoter is preferably seed selective, tissue selective, constitutive, or inducible. The promoter is most preferably the nopaline synthase (NOS), octopine synthase (OCS), mannopine synthase (MAS), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7, wheat POX1, tobacco EIF-4, lectin protein (Le1), or rice RC2 promoter.

Structural Nucleic Acid Sequences in the Recombinant Nucleic Acid Vector

The promoter in the recombinant vector is preferably operably linked to a structural nucleic acid sequence. Exemplary structural nucleic acid sequences, and modified forms thereof, are described in detail above. The promoter of the present invention may be operably linked to a structural nucleic acid sequence that is heterologous with respect to the promoter. In one aspect, the structural nucleic acid sequence may generally be any nucleic acid sequence for which an increased level of transcription is desired. The structural nucleic acid sequence preferably encodes a polypeptide that is suitable for incorporation into the diet of a human or an animal. Suitable structural nucleic acid sequences include those encoding seed storage proteins, herbicide resistance proteins, disease resistance proteins, fatty acid biosynthetic enzymes, tocopherol biosynthetic enzymes, amino acid biosynthetic enzymes, or insecticidal proteins. Preferred structural nucleic acid sequences include, but are not limited to, gamma methyltransferase, phytyl prenyltransferase, beta-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7Sα' seed storage protein, 11S seed storage protein, glycinin, beta-conglycinin, phaseolin, maize globulin-1, maize zeins, seed albumin, and seed lectin.

Alternatively, the promoter and structural nucleic acid sequence may be designed to down-regulate a specific nucleic acid sequence. This is typically accomplished by linking the promoter to a structural nucleic acid sequence that is oriented in the antisense direction. One of ordinary skill in the art is familiar with such antisense technology. Briefly, as the antisense nucleic acid sequence is transcribed, it hybridizes to and sequesters a complimentary nucleic acid sequence inside the cell. This duplex RNA molecule cannot be translated into a protein by the cell's translational machinery. Thus, the cellular complimentary nucleic acid sequence is effectively down regulated as the subsequent steps of translation are disrupted.

Any nucleic acid sequence may be negatively regulated in this manner. Targets of such regulation may include polypeptides that have a low content of essential amino acids, yet are expressed at a relatively high level in a particular tissue. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs.

Recombinant Vectors having Additional Structural Nucleic Acid Sequences

The recombinant vector may also contain one or more additional structural nucleic acid sequences. These additional structural nucleic acid sequences may generally be any sequences suitable for use in a recombinant vector. Such structural nucleic acid sequences include any of the structural nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e. a single operon).

The additional structural nucleic acid sequences preferably encode seed storage proteins, herbicide resistance proteins, disease resistance proteins, fatty acid biosynthetic enzymes, tocopherol biosynthetic enzymes, amino acid biosynthetic enzymes, or insecticidal proteins. Preferred structural nucleic acid sequences include, but are not limited to, gamma methyltransferase, phytyl prenyltransferase, beta-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7Sα' seed storage protein, 11S seed storage protein, glycinin, beta-conglycinin, phaseolin, maize globulin-1, maize zeins, seed albumin, and seed lectin.

Alternatively, the second structural nucleic acid sequence may be designed to down-regulate a specific nucleic acid sequence. This is typically accomplished by operably linking the second structural amino acid, in an antisense orientation, with a promoter. One of ordinary skill in the art is familiar with such antisense technology. The process is also briefly described above. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs.

Selectable Markers

The recombinant vector may further comprise a selectable marker. The nucleic acid sequence serving as the selectable marker functions to produce a phenotype in cells which facilitates their identification relative to cells not containing the marker.

Examples of selectable markers include, but are not limited to: a neo gene (Potrykus, et al., 1985), which codes for kanamycin resistance and can be selected for using kanamycin, G41 8, etc.; a bar gene which codes for bialaphos resistance; a mutant EPSP synthase gene (Hinchee, et al., 1988) which encodes glyphosate resistance; a nitrilase gene which confers resistance to bromoxynil (Stalker et al., 1988); a mutant acetolactate synthase gene (ALS) which confers imidazolinone or sulphonylurea resistance (European Patent Application No. 0154204); green fluorescent protein (GFP); and a methotrexate resistant DHFR gene (Thillet et al., 1988).

Other exemplary selectable markers include: a β-glucuronidase or uidA gene (GUS), which encodes an enzyme for which various chromogenic substrates are known (Jefferson (I), 1987; Jefferson (II), et al., 1987); an R-locus gene, which encodes a product that regulates the production of anthocyanin pigments (red color) in plant tissues (Dellaporta et al., 1988); a β-lactamase gene (Sutcliffe et al., 1978), which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase that can convert chromogenic catechols; an α-amylase gene (Ikatu et al., 1990); a tyrosinase gene (Katz et al., 1983), which encodes an enzyme capable of oxidizing tyrosine to DOPA and dopaquinone (which in turn condenses to melanin); and an α-galactosidase, which will turn a chromogenic α-galactose substrate.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

Other Elements in the Recombinant Vector

Various cis-acting untranslated 5' and 3' regulatory sequences may be included in the recombinant nucleic acid vector. Any such regulatory sequences may be provided in a recombinant vector with other regulatory sequences. Such combinations can be designed or modified to produce desirable regulatory features. Exemplary combinations of regulatory sequences include, but are not limited to, those listed in Table 2.

A 3' non-translated region typically provides a transcriptional termination signal, and a polyadenylation signal which functions in plants to cause the addition of adenylate nucleotides to the 3' end of the mRNA. These may be obtained from the 3' regions to the nopaline synthase (nos) coding sequence, the soybean 7Sα' storage protein coding sequence, the Arcelin-5 coding sequence, the albumin coding sequence, and the pea ssRUBISCO E9 coding sequence. Particularly preferred 3' nucleic acid sequences include Arcelin-5 3', nos 3', E9 3', adr12 3', 7Sα' 3', 11S 3', U.S. Pat. No. 3', and albumin 3'.

Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'.

The recombinant vector may further comprise a nucleic acid sequence encoding a transit peptide. This peptide may be useful for directing a protein to the extracellular space, a chloroplast, or to some other compartment inside or outside of the cell. (see, e.g., European Patent Application Publication Number 0218571)

The structural nucleic acid sequence in the recombinant vector may comprise introns. The introns may be heterologous with respect to the structural nucleic acid sequence. Preferred introns include the rice actin intron and the corn HSP70 intron.

Transgenic Plants and Transformed Host Cells

The invention is also directed to transgenic plants and transformed host cells which comprise, in a 5' to 3' orientation, a promoter operably linked to a heterologous structural nucleic acid sequence. Other nucleic acid sequences may also be introduced into the plant or host cell along with the promoter and structural nucleic acid sequence. These other sequences may include 3' transcriptional terminators, 3' polyadenylation signals, other untranslated nucleic acid sequences, transit or targeting sequences, selectable markers, enhancers, and operators.

Preferred nucleic acid sequences of the present invention, including recombinant vectors, structural nucleic acid sequences, promoters, and other regulatory elements, are described above. The promoter preferably has a nucleic acid sequence that hybridizes under stringent conditions with SEQ ID NO: 1, or the complement thereof; or is at least 94% identical to SEQ ID NO: 1. In another embodiment, the promoter has a nucleic acid sequence that hybridizes under stringent conditions with SEQ ID NO: 2, or the complement thereof; or is at least 94% identical to SEQ ID NO: 2. In another embodiment, the promoter has a nucleic acid sequence that hybridizes under stringent conditions with SEQ ID NO: 14, or the complement thereof, or is at least 94% identical to SEQ ID NO: 14.

Means for preparing such recombinant vectors are well known in the art. For example, methods for making recombinant vectors particularly suited to plant transformation are described in U.S. Pat. Nos. 4,971,908, 4,940,835, 4,769,061 and 4,757,011. These vectors have also been reviewed (Rodriguez, et al., 1988; Glick, et al., 1993) and are described above.

Typical vectors useful for expression of nucleic acids in cells and higher plants are well known in the art and include vectors derived from the tumor-inducing (Ti) plasmid of *Agrobacterium tumefaciens* (Rogers et al., 1987). Other recombinant vectors useful for plant transformation, have also been described (Fromm et al., 1985). Elements of such recombinant vectors are discussed above.

The transformed host cell may generally be any cell which is compatible with the present invention. The transformed host cell is preferably prokaryotic, more preferably a bacterial cell, even more preferably a Agrobacterium, Bacillus, Escherichia, Pseudomonas cell, and most preferably is an *Escherichia coli* cell.

Alternatively, the transformed host cell is preferably eukaryotic, and more preferably a plant, yeast, or fungal cell. The yeast cell preferably is a *Saccharomyces cerevisiae*, *Schizosaccharomyces pombe*, or *Pichia pastoris*. The plant cell preferably is an alfalfa, apple, banana, barley, bean, broccoli, cabbage, carrot, castorbean, celery, citrus, clover, coconut, coffee, corn, cotton, cucumber, garlic, grape, linseed, melon, oat, olive, onion, palm, parsnip, pea, peanut, pepper, potato, radish, rapeseed, rice, rye, sorghum, soybean, spinach, strawberry, sugarbeet, sugarcane, sunflower, tobacco, tomato, or wheat cell. The transformed host cell is more preferably a canola, maize, or soybean cell; and most preferably a soybean cell.

The soybean cell is preferably an elite soybean cell line. An "elite line" is any line that has resulted from breeding and selection for superior agronomic performance. Examples of elite lines are lines that are commercially available to farmers or soybean breeders such as HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H5889 Roundup Ready™, HARTZ™ variety H5999 Roundup Ready™, HARTZ™ variety H6013 Roundup Ready™, HARTZ™ variety H6255 Roundup Ready™, HARTZ™ variety H6454

Roundup Ready™, HARTZ™ variety H6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, Arkansas, U.S.A.); A0868, AG0901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459 and QP4544 (Asgrow Seeds, Des Moines, Iowa, U.S.A.); DeKalb variety CX445 (DeKalb, Ill.).

The transgenic plant is preferably an alfalfa, apple, banana, barley, bean, broccoli, cabbage, carrot, castorbean, celery, citrus, clover, coconut, coffee, corn, cotton, cucumber, garlic, grape, linseed, melon, oat, olive, onion, palm, parsnip, pea, peanut, pepper, potato, radish, rapeseed, rice, rye, sorghum, soybean, spinach, strawberry, sugarbeet, sugarcane, sunflower, tobacco, tomato, or wheat plant. The transformed host plant is more preferably a canola, maize, or soybean cell; and most preferably a soybean plant.

The transgenic soybean plant is preferably an elite soybean plant. An "elite soybean plant" is any plant that is generated from a soybean line that has been bred and selected for superior agronomic performance. Examples of elite plants include those commercially available to farmers or soybean breeders such as HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™M variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H5889 Roundup Ready™, HARTZ™ variety H5999 Roundup Ready™, HARTZ™ variety H6013 Roundup Ready™, HARTZ™ variety H6255 Roundup Ready™, HARTZ™ variety H6454 Roundup Ready™, HARTZ™ variety H6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, Ark., U.S.A.); A0868, AG0901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459 and QP4544 (Asgrow Seeds, Des Moines, Iowa, U.S.A.); DeKalb variety CX445 (DeKalb, Ill.).

Other Organisms

Any of the above described promoters and structural nucleic acid sequences may be introduced into any cell or organism such as a mammalian cell, mammal, fish cell, fish, bird cell, bird, algae cell, algae, fungal cell, fungi, or bacterial cell. Preferred hosts and transformants include: fungal cells such as Aspergillus, yeasts, mammals (particularly bovine and porcine), insects, bacteria and algae Methods to transform such cells or organisms are known in the art (EP 0238023; Yelton et al., *Proc. Natl. Acad. Sci.* (U.S.A.), 81:1470–1474 (1984); Malardier et al., *Gene*, 78:147–156 (1989); Becker and Guarente, In: Abelson and Simon (eds.,), *Guide to Yeast Genetics and Molecular Biology, Methods Enzymol.*, Vol. 194, pp. 182–187, Academic Press, Inc., New York; Ito et al., *J. Bacteriology*, 153:163 (1983); Hinnen et al., *Proc. Natl. Acad. Sci.* (U.S.A.), 75:1920 (1978); Bennett and LaSure (eds.), *More Gene Manipulations in Fungi*, Academic Press, CA (1991), all of which are herein incorporated by reference in their entirety). Methods to produce proteins of the present invention from such organisms are also known (Kudla et al., *EMBO*, 9:1355–1364 (1990); Jarai and Buxton, *Current Genetics*, 26:2238–2244 (1994); Verdier, *Yeast*, 6:271–297 (1990); MacKenzie et al., *Journal of Gen. Microbiol.*, 139:2295–2307 (1993); Hartl et al., *TIBS*, 19:20–25 (1994); Bergeron et al., *TIBS*, 19:124–128 (1994); Demolder et al., *J. Biotechnology*, 32:179–189 (1994); Craig, *Science*, 260:1902–1903 (1993); Gething and Sambrook, *Nature*, 355:33–45 (1992); Puig and Gilbert, *J. Biol. Chem.*, 269:7764–7771 (1994); Wang and Tsou, *FASEB Journal*, 7:1515–1517 (9193); Robinson et al., *Bio/Technology*, 1:381–384 (1994); Enderlin and Ogrydziak, *Yeast*, 10:67–79 (1994); Fuller et al., *Proc. Natl. Acad. Sci.* (U.S.A.), 86:1434–1438 (1989); Julius et al., *Cell*, 37:1075–1089 (1984); Julius et al., *Cell*, 32:839–852 (1983), all of which are herein incorporated by reference in their entirety).

Method for Preparing Transformed Host Cells

The invention is also directed to a method of producing transformed host cells which comprise, in a 5' to 3' orientation, a promoter operably linked to a heterologous -structural nucleic acid sequence. Other sequences may also be introduced into the host cell along with the promoter and structural nucleic acid sequence. These other sequences may include 3' transcriptional terminators, 3' polyadenylation signals, other untranslated sequences, transit or targeting sequences, selectable markers, enhancers, and operators.

Preferred recombinant vectors, structural nucleic acid sequences, promoters, and other regulatory elements are described above. The promoter preferably has a nucleic acid sequence that hybridizes under stringent conditions with SEQ ID NO: 1, or the complement thereof; or is at least 94% identical to SEQ ID NO: 1. In another embodiment, the promoter preferably has a nucleic acid sequence that hybridizes under stringent conditions with SEQ ID NO: 2, or the complement thereof; or is at least 94% identical to SEQ ID NO: 2. In another embodiment, the promoter preferably has a nucleic acid sequence that hybridizes under stringent conditions with SEQ ID NO: 14, or the complement thereof; or is at least 94% identical to SEQ ID NO: 14.

The method generally comprises the steps of selecting a suitable host cell, transforming the host cell with a recombinant vector, and obtaining the transformed host cell.

There are many methods for introducing nucleic acids into host cells. Suitable methods include bacterial infection (e.g. Agrobacterium), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., 1991).

Technology for introduction of DNA into cells is well known to those of skill in the art. These methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992). Alternatively, nucleic acids can be directly introduced into pollen by directly injecting a plant's reproductive organs (Zhou et al., 1983; Hess, 1987; Luo et al., 1988; Pena et al., 1987). The nucleic acids may also be injected into immature embryos (Neuhaus et al., 1987).

The recombinant vector used to transform the host cell typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated nucleic acid sequences, transit and targeting nucleic acid sequences, selectable markers, enhancers, or operators.

Suitable recombinant vectors, structural nucleic acid sequences, promoters, and other regulatory elements are described above.

The transformed host cell may generally be any cell which is compatible with the present invention. The transformed host cell preferably is prokaryotic, more preferably is a bacterial cell, even more preferably is an *Agrobacterium, Arthrobacter, Azospyrillum, Clavibacter, Escherichia, Pseudomonas, Rhizobacterium* cell, and most preferably is an *Escherichia coli* cell. Alternatively, the transformed host cell preferably is eukaryotic, more preferably is a plant, yeast, or fungal cell, and most preferably is an alfalfa, banana, barley, bean, cabbage, carrot, castorbean, celery, clover, coconut, corn, cotton, cucumber, linseed, melon, olive, palm, parsnip, pea, peanut, pepper, potato, radish, rapeseed, rice, soybean, spinach, sunflower, tobacco, tomato, or wheat plant cell. The transformed host cell is more preferably a canola, maize, or soybean cell; and most preferably a soybean cell. The soybean cell is preferably an elite soybean cell (described above).

Method for Preparing Transgenic Plants

The invention is further directed to a method for preparing transgenic plants comprising, in a 5' to 3' direction, a promoter operably linked to a heterologous structural nucleic acid sequence. Other structural nucleic acid sequences may also be introduced into the plant along with the promoter and structural nucleic acid sequence. These other structural nucleic acid sequences may include 3' transcriptional terminators, 3' polyadenylation signals, other untranslated nucleic acid sequences, transit or targeting sequences, selectable markers, enhancers, and operators.

Preferred recombinant vectors, structural nucleic acid sequences, promoters, and other regulatory elements are described above. The promoter preferably has a nucleic acid sequence that hybridizes under stringent conditions with SEQ ID NO: 1, or the complement thereof; or is at least 94% identical to SEQ ID NO: 1. In another embodiment, the promoter preferably has a nucleic acid sequence that hybridizes under stringent conditions with SEQ ID NO: 2, or the complement thereof; or is at least 94% identical to SEQ ID NO: 2. In another embodiment, the promoter preferably has a nucleic acid sequence that hybridizes under stringent conditions with SEQ ID NO: 14, or the complement thereof; or is at least 94% identical to SEQ ID NO: 14.

The method generally comprises selecting a suitable plant cell, transforming the plant cell with a recombinant vector, obtaining the transformed host cell, and culturing the transformed host cell under conditions effective to produce a plant.

The transgenic plant may generally be any type of plant, preferably is one with agronomic, horticultural, ornamental, economic, or commercial value, and more preferably is an alfalfa, apple, banana, barley, bean, broccoli, cabbage, carrot, castorbean, celery, citrus, clover, coconut, coffee, corn, cotton, cucumber, Douglas fir, Eucalyptus, garlic, grape, Loblolly pine, linseed, melon, oat, olive, onion, palm, parsnip, pea, peanut, pepper, poplar, potato, radish, Radiata pine, rapeseed, rice, rye, sorghum, Southern pine, soybean, spinach, strawberry, sugarbeet, sugarcane, sunflower, Sweetgum, tea, tobacco, tomato, turf, or wheat plant. The transformed plant is more preferably a canola, maize, or soybean cell; and most preferably a soybean plant. The soybean plant is preferably an elite soybean plant. An elite plant is any plant from an elite line. Elite lines are described above.

The regeneration, development, and cultivation of plants from transformed plant protoplast or explants is well taught in the art (Weissbach and Weissbach, 1988; Horsch et al, 1985). In this method, transformants are generally cultured in the presence of a selective media which selects for the successfully transformed cells and induces the regeneration of plant shoots (Fraley et al., 1983). These shoots are typically obtained within two to four months.

The shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant strain employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the nucleic acid sequence encoding the antifungal protein to its progeny. The transgenic plant is preferably homozygous for the nucleic acid encoding the antifungal protein and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, northern blotting, immunoprecipitation, and ELISA.

Fusion Proteins

Any of the above described structural nucleic acid sequences, and modified forms thereof, may be linked with additional nucleic acid sequences to encode fusion proteins.

The additional nucleic acid sequence preferably encodes at least 1 amino acid, peptide, or protein. Production of fusion proteins is routine in the art and many possible fusion combinations exist.

For instance, the fusion protein may provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids.

Alternatively, the fusion may provide regulatory, enzymatic, cell signaling, or intercellular transport functions. For example, a sequence encoding a chloroplast transit peptide may be added to direct a fusion protein to the chloroplasts within a plant cell. Such fusion partners preferably encode between 1 and 1000 additional amino acids, more preferably between 5 and 500 additional amino acids, and even more preferably between 10 and 250 amino acids.

Sequence Analysis

In the present invention, sequence similarity or identity is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith, et al., 1983).

The Sequence Analysis Software Package described above contains a number of other useful sequence analysis tools for identifying homologues of the presently disclosed nucleotide and amino acid sequences. For example, the "BLAST" program (Altschul, et al., 1990) searches for sequences similar to a query sequence (either peptide or nucleic acid) in a specified database (e.g., sequence databases maintained at the National Center for Biotechnology Information (NCBI) in Bethesda, Md., USA); "FastA" (Lipman and Pearson, 1985; see also Pearson and Lipman, 1988; Pearson, et al., 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic acid sequence before performing the comparison).

Probes and Primers

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed.

Use of these probes may greatly facilitate the identification of transgenic plants which contain the presently disclosed promoters and structural nucleic acid sequences. The probes may also be used to screen cDNA or genomic libraries for additional nucleic acid sequences related or sharing homology to the presently disclosed promoters and structural nucleic acid sequences.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g. related nucleic acid sequences from other species).

The short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www.genome.wi.mit.edu/cgi-bin/primer/primer3.cgi), STSPipeline (www-genome.wi.mit.edu/cgi-bin/www.STS_Pipeline), or GeneUp (Pesole et al., 1998), for example, can be used to identify potential PCR primers.

The primer or probe is generally complementary to a portion of a nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may be prepared by direct chemical synthesis, by PCR (U.S. Pat. Nos. 4,683,195, and 4,683,202), or by excising the nucleic acid specific fragment from a larger nucleic acid molecule.

EXAMPLES

The following examples are provided to better illustrate the practice of the present invention and should not be interpreted in any way to limit the scope of the present invention. Those skilled in the art will recognize that various modifications, truncations, etcetera can be made to the methods and genes described herein while not departing from the spirit and scope of the present invention.

Example 1

Production of Arcelin Promoters

Seeds of the *P. vulgaris* exotic genotype G02771 containing the Arcelin-5 seed protein are obtained from the USDA seed stock center (USDA, ARS, Washington State University, Regional Plant Introduction Station, 59 Johnson Hall, P.O. Box 646402, Pullman, Wash., USA 99164–6402). A PCR approach is designed and optimized to obtain fragments from the Arcelin-5 nucleic acid sequence. The following six fragments from Arcelin-5 are obtained:

The promoter region (1.8 Kb); the promoter region upstream of the transcription initiation site (TATA box) (1.7 Kb); the 3'UTR region (terminator) (1.3 Kb); the promoter region with a substituted 5'UTR (dSSU soybean 5'UTR) (1.8 Kb); the genomic clone (4 Kb); and the coding region.

Exotic genotypes containing other Arcelin promoters (e.g., Arcelin-3 (PI 41683), Arcelin-4 (PI 417775), are similarly obtained. The Arcelin-3 and Arcelin-4 promoters are cloned using the PCR approach described above. A sequence alignment comparing the Arcelin-3, -4, and -5 promoter sequences is provided in FIGS. 1 and 4a-e. The Arcelin-3 and Arcelin-4 nucleic acid sequences are 99% identical. The Arcelin-5 promoter nucleic acid sequence is approximately 93% identical to the Arcelin-3 and Arcelin-4 nucleic acid sequences. Specific differences between the nucleic acid sequences are also indicated in FIG. 1.

Figure 6:
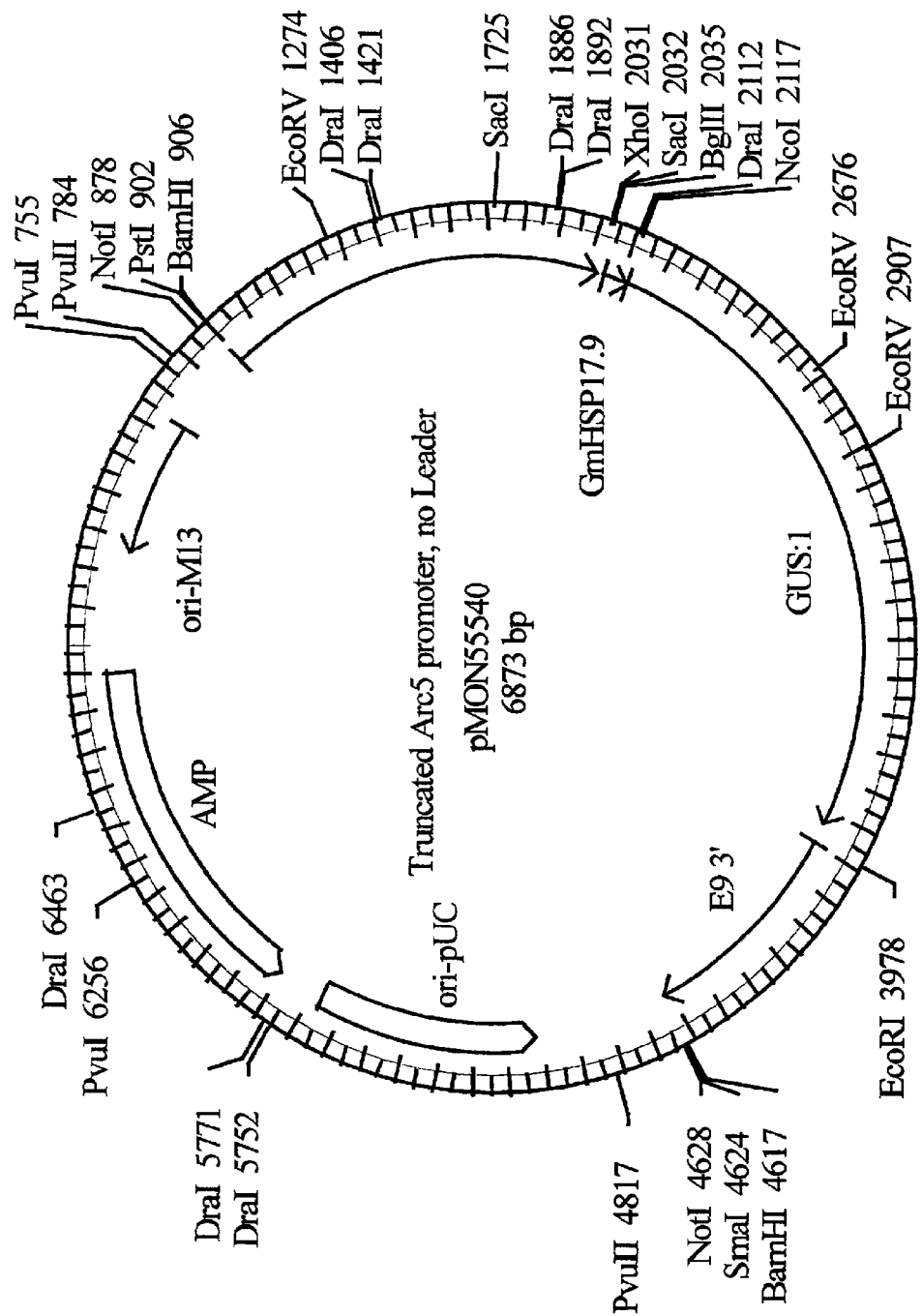
FIG. 6 is a plasmid map showing pMON55540.

A deletion mutant of the Arcelin-5 promoter is also constructed. Approximately 600 base pairs are removed from the promoter nucleic acid sequence. This truncated nucleic acid sequence is designated T-Arc5 (SEQ ID NO: 1). The various Arcelin and 7Sα' promoter constructs are listed in Table 2. The plasmid map for pMON55540, which is a representative construct that can be used for expression of the GUS or Arcelin-5 gene, is shown in FIG. 6. The promoters designated as 7S-1A, 7S-2A, and 7S-3A are those found in U.S. provisional application No. 60/316,975, filed on Sep. 5, 2001 and entitled "Improved Seed Specific 7sα Promoters for Expression of Genes in Plants," which is herein incorporated by reference in its entirety.

with each of the promoter constructs as an internal control. Bombarded tissues are incubated for 48 hours at 25C.

Example 3

Analysis of Arcelin Promoter Activity

Bombarded tissues are analyzed for expression of GUS and luciferase activity. Protein is extracted from six bombarded soybean cotyledons using 1 ml extraction buffer containing 0.1 M potassium phosphate (pH 7.8), 1 0 mM DTT, 1 mM EDTA, 5% glycerol, and protease inhibitor cocktail (1 tablet/50 ml; #1697498, Roche Diagnostics Corporation, Indianapolis, IN). Protein extract is prepared in 100 μl aliquots and tested for luciferase activity according to manufacturer protocol (Steady-Glo™, #E25 10, Promega Corporation, Madison, Wis.). GUS activity is measured using 50 μl aliquots following a standard procedure with minor modification (Maliga, et al., 1995,:Methods in Plant Molecular Biology, A Laboratory Course Manual," Cold Spring Harbor Laboratory Press, page 29). GUS activity is normalized based on the luciferase activity of the internal

TABLE 2

Arcelin and 7Sα' Promoter Constructs

| Plasmid designation | promoter | coding region | 3'UTR | 5'UTR | notes |
|---|---|---|---|---|---|
| pMON13773 (positive control) | 7Sα' | GUS | NOS | native | |
| pMON 55524 | P-PvArc5 | GUS | NOS | native | Arcelin-5 promoter |
| pMON 55525 | P-PvArc5 | GUS | NOS | native | *Arabidopsis* vector |
| pMON 55526 | P-PvArc5 | GUS | NOS | native | Soybean vector |
| pMON 55527 | T-Arc5 | GUS | NOS | native | Truncated Arcelin-5 promoter |
| pMON 55528 | P-PvArc5 | GUS | Arc5 | native | |
| pMON 55529 | T-Arc5 | GUS | NOS | dSSU | |
| pMON 55533 | P-PvArc5 | GUS | E9 | native | |
| pMON 55534 | T-Arc5 | GUS | ADR12 | native | |
| pMON 55535 | T-Arc5 | GUS | E9 | native | |
| pMON 55536 | T-Arc5 | GUS | NOS | PetHSP70 | |
| pMON 55537 | T-Arc5 | GUS | NOS | GmHSP17.9 | |
| pMON 55538 | P-PvArc3 | GUS | NOS | native | Arcelin-3 promoter |
| pMON 55539 | P-PvArc4 | GUS | NOS | native | Arcelin-4 promoter |
| pMON 55540 | T-Arc5 | GUS | E9 | GmHSP17.9 | |
| pMON 55541 | T-Arc5 | GUS | NOS | native | *Arabidopsis* vector |
| pMON 55542 | T-Arc5 | GUS | NOS | native | Soybean vector |
| pMON 55543 | P-PvArc5 | GUS | Arc5 | native | Soybean vector |
| pMON 55544 | P-PvArc5 | GUS | ADR12 | native | |
| pMON 55545 | P-PvArc5 | GUS | Arc5 | native | *Arabidopsis* vector |
| pMON 55546 | 7S-2A | GUS | NOS | native | new 7Sβ promoter |
| pMON 55547 | 7S-3A | GUS | NOS | native | new 7Sβ promoter |
| pMON 55548 | 7S-1A | GUS | NOS | native | new 7Sβ promoter |
| pMON 55S50 | Arcelin-5 | Arc. 5 | Arc5 | Arc5 | *Arabidopsis* vector |
| pMON 55551 | Arcelin-5 | Arc. 5 | Arc5 | Arc5 | Soybean vector |

Example 2

Transformation of Soybean Cotyledons

Soybean cotyledons are transiently transformed with pMON58100, 13773, 55524, 55527, 55538, and 55539 (see Table 2 for description of each) by particle bombardment. Briefly, seeds from Asgrow A3244 soybean plants are harvested 25–28 days after flowering. Seeds are osmotically treated overnight at 25° C. in the dark on Gamborg's Media (G5893, Sigma Aldrich Company, St. Louis, Mo.) supplemented with 50 mM glutamine, 111 mM maltose, 125 mM raffinose, 125 mM mannitol, and 3 g/L purified agar, pH 5.6. The resulting half seeds are bombarded with 2 μg/μl of the Arcelin and 7Sα' promoter constructs. A separate e35S driven luciferase construct is included in a 1:1 molar ratio control. Results of three independent experiments (performed in duplicate) are provided in FIG. 2. The results indicate that the Arcelin-5 promoter is significantly stronger than the bench mark 7Sα' promoter. The Arcelin-3 and Arcelin-4 promoters are at least as strong as the bench mark 7Sα'.

Example 4

Expression from Arcelin Promoters in Transgenic Soybean

To further characterize the Arcelin promoters, multiple transgenic soybean plants are produced containing either the Arcelin-5 promoter/GUS/NOS transgene expression cassette (pMON55526) or the 7Sα' promoter/GUS/NOS transgene expression cassette (pMON39319). Plants are initially screened to exclude those not expressing a transgene. Seventeen lines expressing pMON55526, and 6 lines expressing pMON39319, are assayed for GUS activity.

Briefly, four seeds are chosen from each line and ground to a fine powder. About 20 mg of ground seed powder is mixed with 0.2 ml extraction buffer containing 0.1 M potassium phosphate (pH 7.8), 10 mM DTT, 1 mM EDTA, 5% glycerol, and protease inhibitor cocktail (1 tablet/50 ml; #1697498, Roche Diagnostics Corporation, Indianapolis, IN). The mixtures are incubated at room temperature followed by centrifugation at 6000× g for 20 minutes at 4° C. About 0.1 ml of supernatant is collected and used to measure protein concentration and GUS activity. Protein concentration is measured using the Bio-Rad Protein Assay (#500-0006, Bio-Rad Laboratories, Hercules, Calif.). GUS activity is measured following a standard procedure with a minor modification (Maliga, et al., 1995, Methods in Plant Molecular Biology, A Laboratory Course Manual," Cold Spring Harbor Laboratory Press, page 29).

Figure 3:
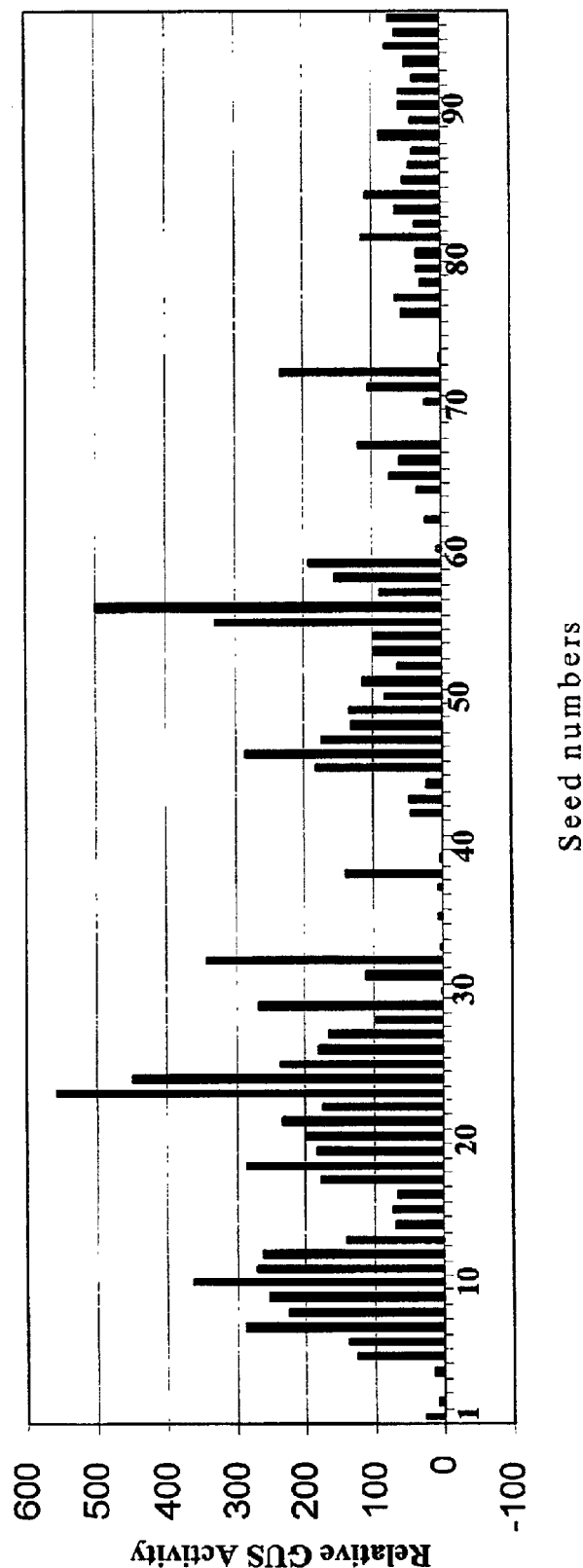
FIG. 3 compares the promoter activities of Arcelin promoters and 7Sα' promoters in transgenic soybean seeds.

FIG. 3 shows the GUS activity of each seed normalized by its respective protein content. Results indicate that the Arcelin-5 promoter is 2 to 4 times stronger than the benchmark 7Sα' promoter.

Example 5

Expression of GUS in Soybean Cotyledons Using a T-Arc5 Promoter

Figure 7:
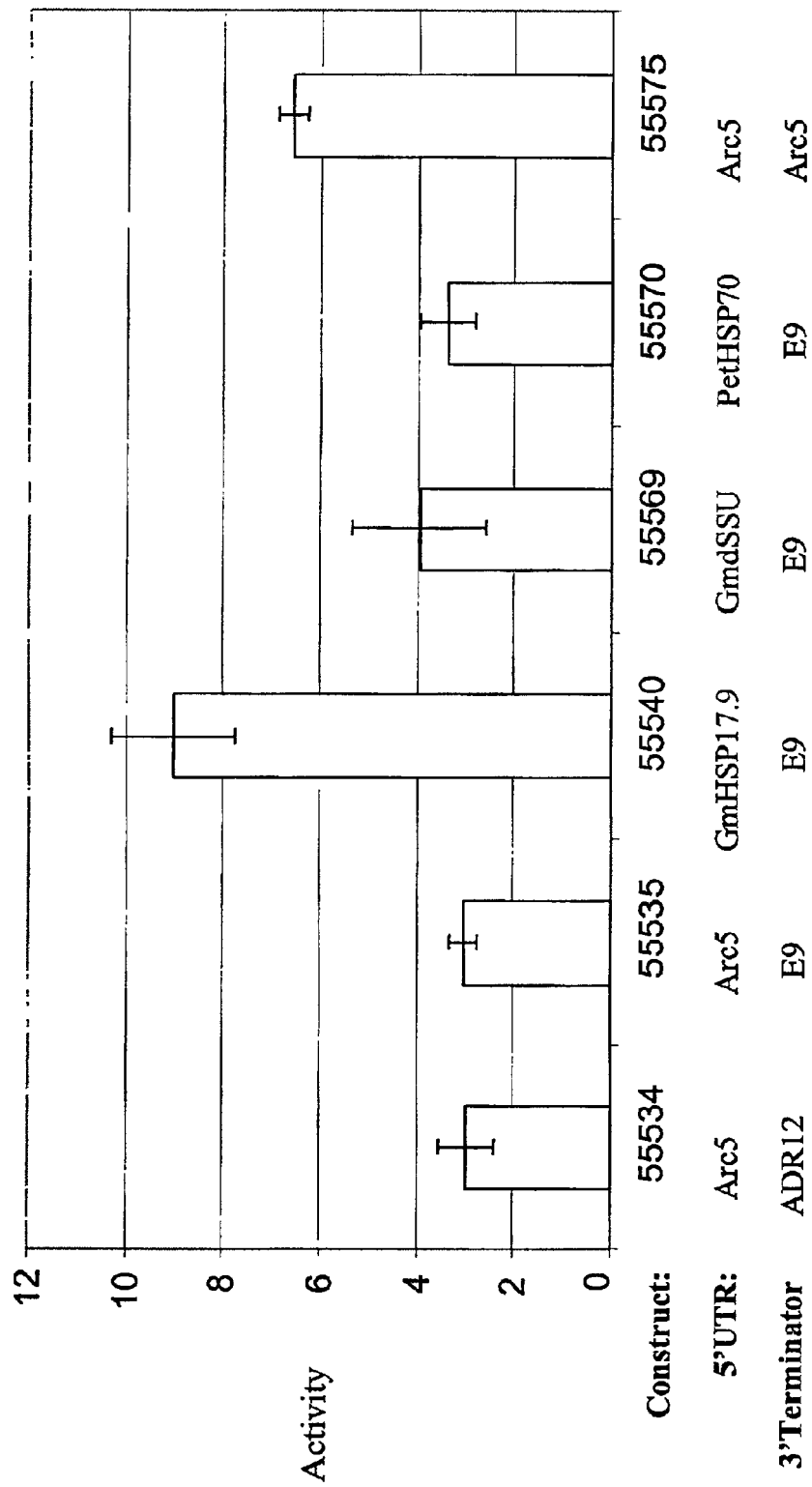
FIG. 7 is a bar graph showing the activity of various constructs having an Arcelin-5 promoter sequence.

Six constructs are tested in soybean cotyledon for expression of the GUS reporter gene. The procedures used for Examples 1–4, above, are used for this example. FIG. 5 shows the six constructs having a T-Arc5 promoter (SEQ ID NO: 2), which is different from the one given above (SEQ ID NO: 1), and a GUS coding sequence. The 5' UTR of the constructs are either GmHSP17.9 (SEQ ID NO: 3), PetHSP70 (SEQ ID NO: 4), GmdSSU (SEQ ID NO: 5) or the Arcelin-5 5' UTR. The 3' terminator is either ADR12 (SEQ ID NO: 6), E9 (SEQ ID NO: 7), or the Arcelin-5 3' terminator (SEQ ID NO: 8). The plasmid map for pMON55540 as shown in FIG. 6 is one example of a vector that can be used to express the constructs shown in FIG. 5 in soybean cotyledons. Results of GUS activity assays are shown in FIG. 7.

While the compositions and methods of this invention have been described in terms of preferred embodiments, it will be apparent to those of skill in the art that variations may be applied to the processes described herein without departing from the concept, spirit and scope of the invention. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

Ainley et al., *Plant Mol. Biol.* 14: 949, 1990.
Altschul, et al., "Basic local alignment search tool." *Journal of Molecular Biology* 215: 403–410, 1990.
Andreas, et al., *Theor. Appl. Genet.*, 72, 123–128, 1986.
Ausubel et al., *Current Protocols in Molecular Biology*, John Wiley and Sons, Inc., 1995.
Battraw and Hall, *Plant Sci.* 86(2):191–202, 1992.
Back et al., *Plant Mol. Biol.* 17: 9, 1991.
Bauer et al., *Gene*, 37: 73, 1985.
Bent et al., *Science*, 265: 1856–1860, 1994.
Bol et al., *Ann. Rev. Phytophathol*, 28: 13–138, 1990.
Bowles, *Ann. Rev. Biochem*, 59: 873–907, 1990.
Braun and Hemenway, *Plant Cell*, 4(6): 735–744, 1992.
Broekaert et al., *Critical Reviews in Plant Sciences*, 16(3): 297–323, 1997.
Bustos, M. M. et al., *EMBO J.* 10: 1469–1479, 1991.
Castresana, C. et al., *EMBO J.* 7: 1929–1936, 1988.
Capecchi, *Cell*, 22(2): 479–488, 1980.
Cashmore et al., Gen. Eng. of Plants, Plenum Press, New York, 29–38, 1983.
Cerda-Olmedo et al., *J. Mol. Biol.* 33: 705–719, 1968.
Chau et al., *Science*, 244:174–181, 1989.
Christensen et al., *Plant Mol. Biol.*, 18: 675,689, 1992.
Christou et al., *Plant Physiol.*, 87: 671–674, 1988.
Christou et al., *Bio/Technology* 9: 957, 1991.
Clapp, *Clin. Perinatol.*, 20(1): 155–168, 1993.
Costa, et al. *Methods Mol. Biol.* 57: 31–44, 1996.
Craik, *BioTechniques*, 3: 12–19, 1985.
Curiel et al., *Hum. Gen. Ther.*, 3(2):147–154, 1992.
Davey et al., *Symp. Soc. Exp. Biol.* 40: 85–120, 1986.
Davey et al., *Plant Mol. Biol.* 13(3): 273–285, 1989.
De Kathen and Jacobsen, *Plant Cell Rep.* 9(5): 276–9, 1990.
Dellaporta et al., Stadler Symposium 11:263–282, 1988.
De la Pena et al., *Nature* 325: 274, 1987.
Deng and Nickloff, *Anal. Biochem.* 200: 81, 1992.
Doyle, J. J. et al., *J. Biol. Chem.* 261: 9228–9238, 1986.
Eglitis and Anderson, *Biotechniques*, 6(7): 608–614, 1988.
Ellis et al., *Proc. Natl. Acad. Sci. U.S.A.*, 92: 4185, 1995.
Feinbaum, R. L. et al., *Mol. Gen. Genet.* 226: 449–456, 1991.
Fitchen and Beachy, *Ann. Rev. Microbiol.* 47: 739–763, 1993.
Fraley et al., *Proc. Natl. Acad. Sci. U.S.A.*, 80: 4803, 1983.
Frits Eckstein et al., *Nucleic Acids Research*, 10: 6487–6497, 1982.
Fromm et al., *Proc. Natl. Acad. Sci. USA*, 82(17): 5824–5828, 1985.
Fromm et al., *Bio/Technology* 8: 833, 1990.
Fynan et al., *Proc. Natl. Acad. Sci. USA*, 90(24): 11478–11482, 1993.
Gasser and Fraley, *Science* 244: 1293, 1989.
Glick, et al. Methods in Plant Molecular Biology and Biotechnology, CRC Press, Boca Raton, Fla., 1993.
Goossens, et al., *Eur. J Biochem.*, 225, 787–95, 1994.
Goossens, et al., *Plant Physiol.*, 120, 1095–1104, 1999.
Gordon-Kamm et al., *Plant Cell*, 2: 603, 1990.
Graham and Van der Eb, *Virology*, 54(2): 536–539, 1973.
Grant, et al., *Plant Cell Rep.* 15(3/4): 254–258 1995.
Grant, et al., *Science*, 269: 843–846, 1995.
Greener, et al. *Mol. Biotechnol.* 7: 189–195, 1997.
Guerola, et al. *Nature New Biol.* 230: 122–125, 1971.
Harlow and Lane, In: *Antibodies: A Laboratory Manual*, Cold Spring Harbor Press, Cold Spring Harbor, N.Y., 1988.
Hershey, H. P. and Stoner, T. D., *Plant Mol. Biol.* 17: 679–690, 1991.
Hess, *Intern Rev. Cytol.*, 107: 367, 1987.
Hinchee, et al., *Bio/Technology* 6:915–922, 1988.
Horsch et al., *Science*, 227: 1229–1231, 1985.
Ikatu et al., *Bio/Technol.* 8:241–242, 1990.
Jefferson (I), *Plant Mol. Biol, Rep.* 5:387–405, 1987.
Jefferson (II), et al, *EMBO J.* 6:3901–3907, 1987.
Johnston and Tang, *Methods Cell Biol.*, 43(A): 353–365, 1994.
Jones et al., *Science*, 266: 789–793, 1994.

Kares et al., *Plant Mol. Biol.* 15: 905, 1990.
Katz et al., *J. Gen. Microbiol.* 129:2703–2714, 1983.
Kawasaki E. S., In: *PCR™ Protocols, A Guide to Methods and Applications*, Innis et al., Eds., Academic Press, San Diego, 21–27, 1990.
Kay, et al., *Science*, 236:1299, 1987.
Keller, et al., *EMBO L.*, 8: 1309–1314, 1989.
Knutzon, et al., *Proc. Natl. Acad. Sci U.S.A.* 89: 2624–2628, 1992.
Koziel et al., *Bio/Technology* 11: 194, 1993.
Kridl et al., *Seed Sci. Res.* 1: 209, 1991.
Kuby, "Immunology," 2d Edition. W. H. Freeman and Company, New York, 1994.
Kuhlemeier, et al., *Plant Cell* 1: 471, 1989.
Kunkel, T. *Proc. Natl. Acad. Sci. U.S.A.*, 82: 488–492, 1985.
Kyte and Doolittle, *J. Mol. Biol.*, 157: 105–132, 1982.
Lam, E. and Chua, N. H., *J. Biol. Chem.* 266: 17131–17135, 1990.
Lam and Chua, *Science* 248: 471, 1991.
Laemmli, *Nature*, 227: 680–685, 1970.
Lioi and Bollini, *Bean Improvement Cooperative*, 32: 28, 1989.
Lipman, D. J. and Pearson, W. R., "Rapid and Sensitive Protein Similarity Searches," *Science*, 227:1435–1441, 1985.
Lindstrom, et al., *Developmental Genetics*, 11: 160, 1990.
Linthorst, *Crit. Rev. Plant Sci.*, 10: 123–150, 1991.
Logemann, et al., *Plant Cell*, 1: 151–158, 1989.
Lu, et al., *J. Exp. Med.*, 178(6): 2089–2096, 1993.
Luo, et al., *Plant Mol Biol. Reporter*, 6: 165, 1988.
Maloy, et al., "Microbial Genetics" $2^{nd}$ Edition, Jones and Barlett Publishers, Boston, Mass., 1994.
Mandel, et al., *Plant Mol. Biol*, 29: 995–1004, 1995.
McCabe, et al., *Biotechnolgy*, 6: 923, 1988.
McElroy, et al., *Plant Cell*, 2:163–171, 1990.
Needleman, S. B. and Wunsch, C. D., "A General Method Applicable to the Search for Similarities in the Amino Acid Sequence of Two Proteins," *Journal of Molecular Biology* 48:443–453, 1970.
Neuhaus, et al., *Theor. Appl. Genet.*, 75: 30, 1987.
Odell, et al., *Nature*, 313: 810, 1985.
Osborn, et al., *Theor. Appl. Genet.*, 71, 847–55, 1986.
Osuna, et al., *Critical Reviews In Microbiology*, 20: 107–116, 1994.
Ou-Lee, et al., *Proc. Natl. Acad. Sci U.S.A.* 83: 6815, 1986.
Ow, et al., *Science* 234:856–859, 1986.
Pearson, W. R. and Lipman, D. J. (1988). Improved Tools for Biological Sequence Analysis. *Proceedings of the National Academy of Sciences USA* 85, 2444–2448.
Pearson, W. R., "Rapid and Sensitive Sequence Comparison with FASTP and FASTA." In *Methods in Enzymology*, (R. Doolittle, ed.), 183, 63–98, Academic Press, San Diego, Calif., USA, 1990.
Pearson, W. R. (1995). Comparison of Methods for Searching Protein Sequence Databases. *Protein Science* 4, 1145–1160.
Pena, et al., *Nature*, 325: 274, 1987.
Perlak, et al., *Bio/Technology*, 8: 939–943, 1990.
Perlak, et al., *Plant Molecular Biology*, 22: 313–321, 1993.
Pesole, et al., *BioTechniques* 25:112–123, 1998
Poszkowski, et al., *EMBO J*, 3: 2719, 1989.
Potrykus, et al., *Ann. Rev. Plant Physiol. Plant Mol. Biol.*, 42: 205, 1991.
Potrykus, et al., *Mol. Gen. Genet.* 199:183–188, 1985.
Pyee, et al., *Plant J.*, 7: 49–59, 1995.
Rhodes, et al., *Science* 240: 204, 1988.
Richins, et al., *Nucleic Acids Res.* 20: 8451, 1987.
Rodriguez, et al. *Vectors: A Survey of Molecular Cloning Vectors and Their Uses*, Butterworths, Boston, 1988.
Rogan and Bessman, *J. Bacteriol.* 103: 622–633, 1970.
Rogers, et al., *Meth. In Enzymol*, 153: 253–277, 1987.
Samac, et al., *Plant Cell*, 3:1063–1072, 1991.
Sambrook, et al., *Molecular Cloning: A Laboratory Manual*, Second Edition, Cold Spring Harbor Laboratory Press, Cold Spring Harbor, N.Y., 1989.
Schroeder, et al., *Plant J.*, 2: 161–172, 1992.
Schroeder, et al., *Plant Physiol.* 101(3): 751–757, 1993.
Schulze-Lefert, et al., *EMBO J.* 8: 651, 1989.
Simpson, *Science*, 233: 34, 1986.
Singer and Kusmierek, *Ann. Rev. Biochem.* 52: 655–693, 1982.
Slighton and Beachy, *Planta* 172: 356, 1987.
Smith, et al, In: *Genetic Engineering: Principles and Methods*, Setlow et al., Eds., Plenum Press, N.Y., 1–32, 1981.
Smith, T. F. and Waterman, M. S., "Comparison of Bio-Sequences," *Advances in Applied Mathematics*, 2:482–489, 1981.
Smith, T. F., Waterman, M. S., and Sadler, J. R., "Statistical Characterization of Nucleic Acid Sequence Functional Domains," *Nucleic Acids Research* 11:2205–2220, 1983.
Somers, et al., *Bio/Technology*, 10: 1589, 1992.
Stalker, et al., *J. Biol. Chem.* 263:6310–6314, 1988.
Sutcliffe et al., *Proc. Natl. Acad. Sci. (U.S.A.)* 75:3737–3741, 1978.
Thillet, et al., *J. Biol. Chem.* 263:12500–12508, 1988.
Vandeyar, et al. *Gene* 65: 129–133, 1988
Van Tunen, et al, *EMBO J.* 7: 1257, 1988.
Vasil, *Biotechnology*, 6: 397, 1988.
Vasil, et al., *Bio/Technology* 10: 667, 1992.
Vodkin, et al., *Cell*, 34: 1023, 1983.
Vogel, et al., *J. Cell Biochem.*, (Suppl) 13D: 312, 1989.
Wagner, et al., *Proc. Natl. Acad. Sci. USA*, 89(13): 6099–6103, 1992.
Watkins, *Handbook of Insecticide Dust Diluents and Carriers*, Second Edition, Darland Books, Caldwell, N.J.
Weissbach and Weissbach, *Methods for Plant Molecular Biology*, (Eds.), Academic Press, Inc., San Diego, Calif., 1988.
Weisshaar, et al., *EMBO J.* 10: 1777–1786, 1991.
Wenzler, et al., *Plant Mol. Biol.*, 12: 41–50, 1989.
Whitham, et al., *Cell*, 78:1101–1115, 1994.
Williams, et al, *Biotechnology* 10: 540–543, 1992.
Winnacker-Kuchler, *Chemical Technology*, Fourth Edition, Volume 7, Hanser Verlag, Munich, 1986.
Wolf, et al., *Compu. Appl. Biosci*, 4(1): 187–91, 1988.
Wong and Neumann, *Biochim. Biophys. Res. Commun.*, 107(2): 584–587, 1982.
Wu, et al., *Plant Cell*, 7(9): 1357–1368, 1995.
Yang, et al., *Proc. Natl. Acad. Sci. USA*, 87: 4144–48, 1990.
Yamaguchi-Shinozaki, et al., *Plant Mol. Biol.* 15: 905, 1990.
Zatloukal, et al., *Ann. N.Y. Acad. Sci.*, 660: 136–153, 1992.
Zhang and Wu, *Theor. Appl. Genet.* 76: 835, 1988.
Zhou, et al., *Methods in Enzymology*, 101: 433, 1983.
Zukowsky, et al., *Proc. Natl. Acad. Sci. (U.S.A.)* 80:1101–1105, 1983.z
U.S. Pat. Nos. 3,959,493; 4,533,557; 4,554,101; 4,683,195; 4,683,202; 4,713,245; 4,757,011; 4,769,061; 4,826,694; 4,940,835; 4,971,908; 5,384,253; and 5,689,052.
European Patent Application Nos. 0154204; 0218571; 0255378; and 0385962.

What is claimed is:

1. A transformed soybean plant cell containing a nucleic acid molecule that comprises in the 5' to 3' direction:
   a promoter comprising the nucleic acid sequence of SEQ ID NO: 1;
   operably linked to a structural nucleic acid sequence;
   wherein the promoter is heterologous with respect to the structural nucleic acid sequence.

2. The transformed soybean plant cell of claim 1, wherein the structural nucleic acid sequence encodes a protein selected from the group consisting of gamma methyltransferase, phytyl prenyltransferase, beta-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7Sα' seed storage protein, 11S seed storage protein, glycinin, beta-conglycinin, phaseolin, maize globulin-1, maize zeins, seed albumin, and seed lectin.

3. The transformed soybean plant cell of claim 1, wherein the nucleic acid molecule further comprises a 5' leader sequence.

4. The transformed soybean plant cell of claim 3, wherein the 5' leader sequence is selected from the group consisting of Arcelin-5 5', dSSU 5', PetHSP70 5', and GmHSP17.9 5'.

5. The transformed soybean plant cell of claim 1, wherein the nucleic acid molecule further comprises a 3' untranslated region.

6. The transformed soybean plant cell of claim 5, wherein the 3' untranslated region is selected from the group consisting of Arcelin-5 3', NOS 3', E9 3', ADR12 3', 7Sα' 3', 11S 3', and albumin 3'.

7. The transformed soybean plant cell of claim 1, wherein the promoter expresses the structural nucleic acid sequence in an amount greater than 2.5% (w/w) of the total cellular RNA or protein.

8. The transformed soybean plant cell of claim 7, wherein the promoter expresses the structural nucleic acid sequence in an amount greater than 5% (w/w) of the total cellular RNA or protein.

9. The transformed soybean plant cell of claim 8, wherein the promoter expresses the structural nucleic acid sequence in an amount greater than 10% (w/w) of the total cellular RNA or protein.

10. A transgenic soybean plant containing a nucleic acid molecule that comprises in the 5' to 3' direction:
   a promoter comprising the nucleic acid sequence of SEQ ID NO: 1;
   operably linked to a structural nucleic acid sequence;
   wherein the promoter is heterologous with respect to the structural nucleic acid sequence.

11. The transgenic soybean plant of claim 10, wherein the promoter is SEQ ID NO: 1.

12. The transgenic soybean plant of claim 10, wherein the structural nucleic acid sequence encodes a protein selected from the group consisting of gamma methyltransferase, phytyl prenyltransferase, beta-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7Sα' seed storage protein, 11S seed storage protein, glycinin, beta-conglycinin, phaseolin, maize globulin-1, maize zeins, seed albumin, and seed lectin.

13. The transgenic soybean plant of claim 10, wherein the nucleic acid molecule further comprises a 5' leader sequence.

14. The transgenic soybean plant of claim 13, wherein the 5' leader sequence is selected from the group consisting of Arcelin-5 5', dSSU 5', PetHSP70 5', and GmHSP17.9 5'.

15. The transgenic soybean plant of claim 10, wherein the nucleic acid molecule further comprises a 3' untranslated region.

16. The transgenic soybean plant of claim 15, wherein the 3' untranslated region is selected from the group consisting of Arcelin-5 3', NOS 3', E9 3', ADR12 3', 7Sα' 3', 11S 3', and albumin 3'.

17. The transgenic soybean plant of claim 10, wherein the promoter expresses the structural nucleic acid sequence in an amount greater than 2.5% (w/w) of the total cellular RNA or protein.

18. The transgenic soybean plant of claim 17, wherein the promoter expresses the structural nucleic acid sequence in an amount greater than 5% (w/w) of the total cellular RNA or protein.

19. The transgenic soybean plant of claim 18, wherein the promoter expresses the structural nucleic acid sequence in an amount greater than 10% (w/w) of the total cellular RNA or protein.

20. The transgenic soybean plant cell of claim 1, wherein the promoter is SEQ ID NO: 1.

* * * * *

SEQUENCE LISTING

<160> NUMBER OF SEQ ID NOS: 14

<210> SEQ ID NO 1
<211> LENGTH: 1148
<212> TYPE: DNA
<213> ORGANISM: Phaseolus vulgaris

<400> SEQUENCE: 1

| | | | | | |
|---|---|---|---|---|---|
| taggatcctt | caatagaaaa | tgtgttattt | cctcatcacc | agacaaaggg | gcaacagtta | 60 |
| acaaaacaaa | tttatgtttc | atttgagatt | aaggaaggta | aggaagaaaa | aagattaaaa | 120 |
| aaaatgtcct | tatctctttg | tttctgtaat | aataatataa | gagacttaaa | cttttaatat | 180 |
| aataattgta | attaggtttt | ctagtcatga | gcaccactca | gagacaagat | ttcaagaaaa | 240 |
| caattttgtt | aaacatctta | ttagaaactt | ttagttaagt | cttgaagtta | gaattaaaca | 300 |
| aaaaaaatta | cacacgagaa | acacaataaa | cccactaccg | tcaggttatc | ataaggatga | 360 |
| aatgttttga | tatcattaaa | tataacacac | acaaaaatac | atctaattat | aacaatatat | 420 |
| gttatacata | tattttgta | aaacttaga | gttttcaaa | acattctaat | acatgattag | 480 |
| agtttataga | aatacaaata | tttaaaaaat | ataatttaa | aaaaacattc | taaagtcatt | 540 |
| cagatcctct | cacacctgtg | tgatcattta | gtcatgtatg | tagtacaatc | attgtagttc | 600 |
| acaacagagt | aaaataaata | aggataaact | agggaatata | tataatatat | acaattaaat | 660 |
| aaaaaaggga | aaatcaaatt | agaattttg | attccccaca | tgacacaact | caccatgcac | 720 |
| gctgccacct | cagctccctc | ctctccacac | atgtctcatg | tcactttcga | ctttggcttt | 780 |
| ttcactatga | cacaactcgc | catgcatgtt | gccacgtgag | ctccttcctc | ttcccatgat | 840 |
| gacaccactg | ggcatgcatg | ctgccacctc | agctcccacc | tcttctcatt | atgagcctac | 900 |
| tggccatgca | cactgccacc | tcagcactcc | tctcacttcc | cattgctacc | tgccaaaccg | 960 |
| cttctctcca | taaatatcta | tttaaattta | aactaattat | ttcatatact | tttttgatga | 1020 |
| cgtggatgca | ttgccatcgt | tgtttaataa | ttgttaattt | ggagttgaat | aataaaatga | 1080 |
| aagaaaaaag | ttggaaagat | tttgcatttg | ttgttgtata | aatagagaag | agagtgatgg | 1140 |
| ttaatgca | | | | | | 1148 |

<210> SEQ ID NO 2
<211> LENGTH: 1122
<212> TYPE: DNA
<213> ORGANISM: Phaseolus vulgaris

<400> SEQUENCE: 2

| | | | | | |
|---|---|---|---|---|---|
| ggatccttca | atagaaaatg | tgttatttcc | tcatcaccag | acaaggggc | aacagttaac | 60 |
| aaaacaaatt | tatgtttcat | ttgagattaa | ggaaggtaag | gaagaaaaa | gattaaaaaa | 120 |
| aatgtcctta | tctctttgtt | tctgtaataa | taatataaga | gacttaaact | tttaatataa | 180 |
| taattgtaat | taggttttct | agtcatgagc | accactcaga | gacaagattt | caagaaaaca | 240 |
| attttgttaa | acatcttatt | agaaactttt | agttaagtct | tgaagttaga | attaaacaaa | 300 |
| aaaattaca | cacgagaaac | acaataaacc | cactaccgtc | aggttatcat | aaggatgaaa | 360 |
| tgttttgata | tcattaaata | taacacacac | aaaaatacat | ctaattataa | caatatatgt | 420 |
| tatacatata | ttttgtaaa | aacttagagt | ttttcaaaac | attctaatac | atgattagag | 480 |
| tttatagaaa | tacaaatatt | taaaaatat | aattttaaaa | aaacattcta | aagtcattca | 540 |
| gatcctctca | cacctgtgtg | atcatttagt | catgtatgta | gtacaatcat | tgtagttcac | 600 |

```
aacagagtaa aataaataag gataaactag ggaatatata taatatatac aattaaataa      660
aaaagggaaa atcaaattag aatttttgat tccccacatg acacaactca ccatgcacgc      720
tgccacctca gctccctcct ctccacacat gtctcatgtc actttcgact ttggcttttt      780
cactatgaca caactcgcca tgcatgttgc cacgtgagct ccttcctctt cccatgatga      840
caccactggg catgcatgct gccacctcag ctcccacctc ttctcattat gagcctactg      900
gccatgcaca ctgccacctc agcactcctc tcacttccca ttgctacctg ccaaaccgct      960
tctctccata aatatctatt taaatttaaa ctaattattt catatacttt tttgatgacg     1020
tggatgcatt gccatcgttg tttaataatt gttaatttgg agttgaataa taaaatgaaa     1080
gaaaaaagtt ggaaagattt tgcatttgtt gttgtataaa ta                        1122
```

<210> SEQ ID NO 3
<211> LENGTH: 76
<212> TYPE: DNA
<213> ORGANISM: Glycine max

<400> SEQUENCE: 3

```
acacagaaac attcgcaaaa acaaaatccc agtatcaaaa ttcttctctt tttttcatat       60
ttcgaaagat ttaaaa                                                       76
```

<210> SEQ ID NO 4
<211> LENGTH: 91
<212> TYPE: DNA
<213> ORGANISM: Petunia sp.

<400> SEQUENCE: 4

```
aacagaaaaa tttgctacat tgtttcacaa acttcaaata ttattcattt atttgtcagc       60
tttcaaactc tttgtttctt gtttgttgat t                                      91
```

<210> SEQ ID NO 5
<211> LENGTH: 15
<212> TYPE: DNA
<213> ORGANISM: Glycine sp.

<400> SEQUENCE: 5

```
ctaagaagaa gaacc                                                        15
```

<210> SEQ ID NO 6
<211> LENGTH: 1123
<212> TYPE: DNA
<213> ORGANISM: Glycine sp.

<400> SEQUENCE: 6

```
tgagggcatg cacgcacggc ctcggagggg aaccagaaaa ttatgttaac aaaataatct       60
ggaaccctaa tgtatcagtg tcatcatcag tgtgtagttt aagctagctt tgctatggtt      120
acgttctctg agatgagagt cttgatgaac agtgccattc tgatgtattg ctttccttga      180
aagttaatgc atgcttctta tcttctgtct atagctatat gctttctttt tcttttctt      240 ttttgttaat cagaacattt gcaacttcac tccttagtat ataatagtta tccatacaaa      300
aagaaatatt atttaaggac atactgaaac ataaatatta cacttttttag catccataaa     360 aaaaaattga acgaggaggg ttaaaaatat atttttaaca ttttttttaat atattctttg     420 ttattgattg aatttaaaaa aaaatataaa attagctaga gagaaaatta ttaaataaaa      480 tataacccctt aaaatttat aatatttaat aaattttaat caattaaaaa gaacactcct      540
ccagacttaa gatttggggt atggattaat tcactagtaa gtacatcatt aagattcatt      600
```

-continued

```
cgattcaatg cagcggacaa gggaaataaa agaaaatact atatgtgggt ttttttacta      660
caagaaatat tatctatgtc tacgacaaaa aaccatcact agatgttaaa aatgtgtagg      720
taaatataat aaaaattttg tcctacagac attgtggtcg tcaactttga ggggacgcat      780
gtgacaccct ctatccctca catatatact aacaaaggaa taaaaattca aatattaatt      840
aaagtatttt tttttgaaca tttttaaata cgggtctttc aaagggataa aaggttcaca      900
atcactttct tctacatcat attcaaactt gtccaaataa ataataaagt catcggctcg      960
aacaaggtcg tttgagactt catacaatta atataaaacc ctatacccca atgtcacatc     1020
ctatcagagc gttgtgtctc gacgtctttc agcacaatat tccttaaagc agtttaccta     1080
gtcatcttgc tcccccgaac acagagtcca agatcatcac agg                       1123

<210> SEQ ID NO 7
<211> LENGTH: 632
<212> TYPE: DNA
<213> ORGANISM: Pisum sp.

<400> SEQUENCE: 7
gctttcgttc gtatcatcgg tttcgacaac gttcgtcaag ttcaatgcat cagtttcatt       60
gcgcacacac cagaatccta ctgagttcga gtattatggc attgggaaaa ctgttttttct     120 tgtaccattt gttgtgcttg taatttactg tgttttttat tcggttttcg ctatcgaact      180
gtgaaatgga aatggatgga gaagagttaa tgaatgatat ggtccttttg ttcattctca      240
aattaatatt atttgttttt tctcttattt gttgtgtgtt gaatttgaaa ttataagaga      300
tatgcaaaca ttttgttttg agtaaaaatg tgtcaaatcg tggcctctaa tgaccgaagt      360
taatatgagg agtaaaacac ttgtagttgt accattatgc ttattcacta ggcaacaaat      420
atattttcag acctagaaaa gctgcaaatg ttactgaata caagtatgtc ctcttgtgtt      480
ttagacattt atgaactttc ctttatgtaa ttttccagaa tccttgtcag attctaatca      540
ttgctttata attatagtta tactcatgga tttgtagttg agtatgaaaa tatttttaa       600 tgcattttat gacttgccaa ttgattgaca ac                                    632

<210> SEQ ID NO 8
<211> LENGTH: 1259
<212> TYPE: DNA
<213> ORGANISM: Phaseolus vulgaris

<400> SEQUENCE: 8
actcccaaaa ccaccttccc tgtgacagtt aaaccctgct tataccttc ctcctaataa        60 tgttcatctg tcacacaaac taaaataaat aaaatgggag caataaataa aatgggagct     120
catatattta caccatttac actgtctatt attcaccatg ccaattatta cttcataatt      180
ttaaaattat gtcatttta aaaattgctt aatgatggaa aggattatta taagttaaaa      240
gtataacata gataaactaa ccacaaaaca aatcaatata aactaactta ctctcccatc     300
taatttttat ttaaatttct ttacacttct cttccatttc tatttctaca acattattta      360
acatttttat tgtattttc ttactttcta actctattca tttcaaaaat caatatatgt      420
ttatcaccac ctctctaaaa aaaactttac aatcattggt ccagaaaagt taaatcacga     480
gatggtcatt ttagcattaa acaacgatt cttgtatcac tatttttcag catgtagtcc      540
attctcttca aacaaagaca gcggctatat aatcgttgtg ttatattcag tctaaaacaa      600
ttgttatggt aaaagtcgtc attttacgcc ttttttaaaag atataaaatg acaattatgg     660
ttaaaagtca tcatgttaga tcctccttaa agatataaaa tgacagtttt gataaaaagt     720
```

-continued

```
ggtcatttta tacgctcttg aaagatataa aacgacggtt atggtaaaag ctgccatttt      780
aaatgaaata ttttttgtttt agttcatttt gtttaatgct aatcccattt aaattgactt     840
gtacaattaa aactcaccca cccagataca atataaacta acttactctc acagctaagt     900
tttatttaaa tttctttaca cttctttttcc atttctattt ctatgacatt aactaacatt     960
tttctcgtaa ttttttttct tattttctaa ctctatccat ttcaaatcga tatatgttta    1020
tcaccaccac tttaaaaaga aaatttacaa tttctcgtgc aaaaaagcta aatcatgacc    1080
gtcattttag cattaaaaca acgattcttg tatcgttgtt tttcagcatg tagtccattc    1140
ttttcaagca aagacaacag ctatataatc atcgtgttat attcagtcta aaacaacagt    1200
aatgataaaa gtcatcattt taggcctttc tgaaatatat agaacgacat tcatggtaa     1259
```

<210> SEQ ID NO 9
<211> LENGTH: 322
<212> TYPE: DNA
<213> ORGANISM: Phaseolus vulgaris

<400> SEQUENCE: 9

```
attgtttcac ctacaatgat aatatattaa aaagtgaact ttaaattaat ttacaagtta      60
aattaattca gcttgtctcc ttgatgttta tgctcttttc ggaattaatt aagttttagt     120
tgtaattgta ataattagtc acgagtgtgt atcctcaccc ctcacaaaca catttcaag     180 aaaaataaaa ttttataaaa agggaaaatc aaattagaat ttcgttgttt gttaattgtt     240
aattttatat tattatttct ccctcaaata atattataaa agataatgat tcgattttga     300 ttttgcatttt gttgttgtat aa                                              322
```

<210> SEQ ID NO 10
<211> LENGTH: 316
<212> TYPE: DNA
<213> ORGANISM: Phaseolus vulgaris

<400> SEQUENCE: 10

```
attgtttcac ctacaatgat aatatattaa aaagtgaact ttaaattaat ttacaagtta      60
aattaattca gcttgtctcc ttgatgttta tgctcttttc ggaattaatt aagttttagt     120
tgtaattgta ataattagtc acgagtgtgt atcctcaccc ctcacaaaca catttcaag     180 aaaaataaaa ttttataaaa agggaaaatc aaattagaat ttcgttgttt gttaattgtt     240
aattttatat tattatttct ccctcaaata atattataaa agataatgat tcgattttgc     300
atttgttgtt gtataa                                                     316
```

<210> SEQ ID NO 11
<211> LENGTH: 288
<212> TYPE: DNA
<213> ORGANISM: Phaseolus vulgaris

<400> SEQUENCE: 11

```
attttttttca catacaatta tgataatata ttaaaaagtg aactttaaat taatttacaa      60
tatatagatt cagttaaatc aattcagctt gtctccttga tgtttctgta ataactagtc     120
atgagcacca ctcagagaca agatttcaag aaaaatatat aatatataca attaaataaa     180
aaagggaaaa tcaaattaga atttcgttgt ttaataattg ttaatttgga gttgaataat     240
aaaatgaaag aaaaaagttg gaaagatttt gcatttgttg ttgtataa                   288
```

<210> SEQ ID NO 12
<211> LENGTH: 1872
<212> TYPE: DNA
<213> ORGANISM: Phaseolus vulgaris

<400> SEQUENCE: 12

```
ctgcagtcct acataattct tctaccgtta accgtcaaat catattttca ttattcacaa      60
atatctagta tctcatacga ataaatatat attgtttcac ctacaatgat aatatattaa     120
aaagtgaact ttaaatgtaa tttaatctca taaaatcgac ttataaaatg agatttatac     180
ctacgatcga taaaaataac tttaatatca tattaagaaa taaactttaa acctaactca     240
atttatataaa accaatttat aaaataaaat ttacactcac ttatatatta taaaataaaa    300
tagttttttag gtgacgtgaa atctccatcc gattaatcaa tattttctga tgttattgtt    360
attatagaaa ctaaaaacat gccaaataat ttacaagtta aattaattca gcttgtctcc    420
ttgactaata aaacacaact ttagactatt attcagattt acacttcatc tctcatgata    480
tccctcaaag tgaatttcat tcatggcacc atttatataa tcaacaattt taaaaagatg   540
caaatttgta ctagtaaatg cttcaatgtc cctgataaac acacacaaaa aaaccttttc    600
atatttttt cttattaaat aaagaaattc attgtaagag aaattaggat ccttcaatag    660
aaaatgtgtt atttcctcat caccaggaaa aaaggacaa cagttaacac aacaaattta     720
tgtttcattt gagattaagg aaggtaagga agaaaaaaga ttaaaaaaaa tgtcctatc     780
tctttgttta tgctcttttc ggaattaatt aagttttagt tgtaattgta ataataatat     840
aagagactta aacttttaat ataataatta taattaggtt tttttttagtc acgagtgtgt    900
atcctcaccc ctcacaaaca acatttcaag aaaacaattt tgttaaacat cttattagaa    960
acttttagca aagtcttgaa gttagaatta acaaaaaat ttacacacac gaggaacaca    1020
ataaacctac tatcgtcagg ttatcataag gatgaaatgt tttgatacca ttaaatataa   1080
cacacacaaa aatacatgta attataacaa tacatgttat acatattttt gaaaaaactt    1140
aaagtttttc aaaacattct taatacatga ttagagctta tagaaataca aatatttaaa   1200
aaatataact ttaaaaaaac atcttaaagt cctcatatcc tctcacaccg gtgaaatcat   1260
ttactcgtag tatagtaccg tgtcataata gttcacaaca cagtaaaaag aataagaata   1320
aactagtgaa tataaaattt tataaaaagg gaaaatcaaa ttagaatttt tgattcccca    1380
cataacacaa ctcaccatgc acgctgccac ctcagctccc tcctctccac acatgtctca   1440
tgtcactttc gactttggct ttttcactag gagacaactc gccatgcacg ctgccacgtc    1500
agctccttcc tcttcccatg atgacaccac tgggcatgca tgatgccacc tcagctccca    1560
cctcttctca ttatgagcct actggccatg cacactgcca cctcagcact cctctcactt   1620
cccattgcta cctgccaaac cgcttctctc tataaatatc tctttaaatt taaactaatt    1680
atttcatata cttttttgat gacgtggatg cattgccatc gttgtttgtt aattgttaat    1740
tttatattat tatttctccc tcaaataata ttataaaaga taatgattcg attttgattt    1800
tgcatttgtt gttgtataaa tagagaagag agtgatggtt aatgcatgaa tgcatgatca    1860
gatctgccat gg                                                         1872
```

<210> SEQ ID NO 13
<211> LENGTH: 1866
<212> TYPE: DNA
<213> ORGANISM: Phaseolus vulgaris

<400> SEQUENCE: 13

```
ctgcagtcct acataattct tctaccgtta accgtcaaat catattttca ttattcacaa      60
atatctagtg tctcatacga ataaatatat attgtttcac ctacaatgat aatatattaa     120
aaagtgaact ttaaatgtaa tttaatctca taaaatcgac ttataaaatg agatttatac     180
ctacgatcga taaaaataac tttaatatca tattaagaaa taaactttaa acctaactca     240
attttataaa accaatttat aaaataaaat ttacactcac ttatatatta taaaataaaa     300
tagttttttag gtgacgtgaa atctccatcc gattaatcaa tattttctga tgttattgtt     360
attatagaaa ctaaaaacat gccaaataat ttacaagtta aattaattca gcttgtctcc     420
ttgactaata aaacacaact ttagactatt attcagattt acacttcatc tctcatgata     480
tccctcaaag tgaatttcat tcatggcacc atttatataa tcaacaattt taaaaagatg     540
caaatttgta ctagtaaatg cttcaatgtc cctgataaac acacacaaaa aaaccttttc     600
atattttttt cttattaaat aaagaaattc attgtaagag aaattaggat ccttcaatag     660
aaaatgtgtt atttcctcat caccaggaaa aaaggacaa cagttaacac aacaaattta     720
tgtttcattt gagattaagg aaggtaagga agaaaaaaga ttaaaaaaaa tgtccttatc     780
tctttgttta tgctcttttc ggaattaatt aagttttagt tgtaattgta ataataatat     840
aagagactta aactttaat ataataatta taattaggtt ttttttagtc acgagtgtgt     900
atcctcaccc ctcacaaaca acatttcaag aaaacaattt tgttaaacat cttattagaa     960
acttttagca aagtcttgaa gttagaatta acaaaaaaat ttacacacac gaggaacaca    1020
ataaacctac tatcgtcagg ttatcataag gatgaaatgt tttgatacca ttaaatataa    1080
cacacacaaa aatacatgta attataacaa tacatgttat acatattttt gaaaaaactt    1140
aaagttttttc aaaacattct taatacatga ttagagctta tagaaataca aatatttaaa    1200
aaatataact ttaaaaaaac atcttaaagt cctcatatcc tctcacaccg gtgaaatcat    1260
ttactcgtag tatagtaccg tgtcataata gttcacaaca cagtaaaaag aataagaata    1320
aactagtgaa tataaaattt tataaaaagg gaaaatcaaa ttagaatttt tgattcccca    1380
cataacacaa ctcaccatgc acgctgccac ctcagctccc tcctctccac acatgtctca    1440
tgtcactttc gactttggct ttttcactag gagacaactc gccatgcacg ctgccacgtc    1500
agctccttcc tcttcccatg atgacaccac tgggcatgca tgatgccacc tcagctccca    1560
cctcttctca ttatgagcct actggccatg cacactgcca cctcagcact cctctcactt    1620
cccattgcta cctgccaaac cgcttctctc tataaatatc tctttaaatt taaactaatt    1680
atttcatata cttttttgat gacgtggatg cattgccatc gttgtttgtt aattgttaat    1740
tttatattat tatttctccc tcaaataata ttataaaaga taatgattcg atttttgcatt    1800
tgttgttgta taaatagaga agagagtgat ggttaatgca tgaatgcatg atcagatctg    1860
ccatgg                                                                1866
```

<210> SEQ ID NO 14
<211> LENGTH: 1832
<212> TYPE: DNA
<213> ORGANISM: Phaseolus vulgaris

<400> SEQUENCE: 14

```
ctgcagtcct acataattct tctacagtta accttcaaat catattttca ttattcacaa      60
atatctagtc attcatacga ataaatatat attttttttca catacaatta tgataatata     120
ttaaaaagtg aactttaaat ttaatttaat cttataaaat caacttataa aatgagattt     180
```

-continued

```
ctacctacga ttaataaaaa taactttgat atcatattaa aaaataaact ttaaacctaa      240
ctcaacttta taaaaccaat ttataaaata aaatttacac tcagttatga attataaaat      300
gaaatagttt ttaggtgacg tggaatctcc atccgattaa tcaatatttg atgatgttat      360
tgttattata gaaactaaaa acatgccaaa taatttacaa tatatagatt cagttaaatc      420
aattcagctt gtctccttga ctaataaaaa aaaactttag actattattc agatttacac      480
ttcatctctc atgatatccc tcaaagtgaa tttcattcat ggcaccattt atataatcaa      540
caattttaaa aatatgcaaa tttgtaccag taaatgcttt aatgtccctg ataaacacaa      600
aaaaaaaaaa attcatattt ttttcttatt aaataaagaa gttcattgta agagaaatta      660
ggatccttca atagaaaatg tgttatttcc tcatccaccag acaaaggggc aacagttaac     720
aaaacaaatt tatgtttcat ttgagattaa ggaaggtaag gaagaaaaaa gattaaaaaa     780
aatgtcctta tctctttgtt tctgtaataa taatataaga gacttaaact tttaatataa     840
taattgtaat taggttttct agtcatgagc accactcaga gacaagattt caagaaaaca     900
attttgttaa acatcttatt agaaactttt agttaagtct tgaagttaga attaaacaaa     960
aaaaattaca cacgagaaac acaataaacc cactaccgtc aggttatcat aaggatgaaa    1020
tgttttgata tcattaaata taacacacac aaaaatacat ctaattataa caatatatgt    1080
tatacatata tttttgtaaa aacttagagt ttttcaaaac attctaatac atgattagag    1140
tttatagaaa tacaaatatt taaaaaatat aattttaaaa aaacattcta aagtcattca    1200
gatcctctca cacctgtgtg atcatttagt catgtatgta gtacaatcat tgtagttcac    1260
aacagagtaa aataaataag gataaactag ggaatatata taatatatac aattaaataa    1320
aaaagggaaa atcaaattag aatttttgat tccccacatg acacaactca ccatgcacgc    1380
tgccacctca gctccctcct ctccacacat gtctcatgtc actttcgact ttggcttttt    1440
cactatgaca caactcgcca tgcatgttgc cacgtgagct ccttcctctt cccatgatga    1500
caccactggg catgcatgct gccacctcag ctcccacctc ttctcattat gagcctactg    1560
gccatgcaca ctgccacctc agcactcctc tcacttccca ttgctacctg ccaaaccgct    1620
tctctccata aatatctatt taaatttaaa ctaattattt catatacttt tttgatgacg    1680
tggatgcatt gccatcgttg tttaataatt gttaatttgg agttgaataa taaaatgaaa    1740
gaaaaaagtt ggaaagattt tgcatttgtt gttgtataaa tagagaagag agtgatggtt    1800
aatgcatgaa tgcatgatca gatctgccat gg                                  1832
```